US010629046B2

(12) United States Patent
Kusens

(10) Patent No.: US 10,629,046 B2
(45) Date of Patent: Apr. 21, 2020

(54) SYSTEMS AND METHODS FOR DETERMINING WHETHER AN INDIVIDUAL ENTERS A PRESCRIBED VIRTUAL ZONE USING SKELETAL TRACKING AND 3D BLOB DETECTION

(71) Applicant: CERNER INNOVATION, INC., Kansas City, KS (US)

(72) Inventor: Neil Kusens, Sherman Oaks, CA (US)

(73) Assignee: CERNER INNOVATION, INC., Kansas, KS (US)

( * ) Notice: Subject to any disclaimer, the term of this patent is extended or adjusted under 35 U.S.C. 154(b) by 0 days.

(21) Appl. No.: 16/166,857

(22) Filed: Oct. 22, 2018

(65) Prior Publication Data

US 2019/0057592 A1    Feb. 21, 2019

Related U.S. Application Data

(63) Continuation of application No. 15/728,110, filed on Oct. 9, 2017, now Pat. No. 10,147,297, which is a (Continued)

(51) Int. Cl.
*G06K 9/00* (2006.01)
*G08B 21/04* (2006.01)
(Continued)

(52) U.S. Cl.
CPC .......... *G08B 21/043* (2013.01); *A61B 5/1117* (2013.01); *A61B 5/1128* (2013.01);
(Continued)

(58) Field of Classification Search
CPC .................................. G06K 9/00; G06T 7/00
(Continued)

(56) References Cited

U.S. PATENT DOCUMENTS 4,669,263 A    6/1987  Sugiyama
4,857,716 A    8/1989  Gombrich et al.
(Continued)

FOREIGN PATENT DOCUMENTS

| DE | 19844918 A1 | 4/2000 |
|---|---|---|
| WO | 2009/018422 A1 | 2/2009 |
| WO | 2012/122002 A1 | 9/2012 |

OTHER PUBLICATIONS

Notice of Allowance received for U.S. Appl. No. 15/857,696, dated Jul. 16, 2019, 9 pages.
(Continued)

*Primary Examiner* — Abolfazl Tabatabai
(74) *Attorney, Agent, or Firm* — Shook, Hardy & Bacon, LLP

(57) ABSTRACT

A method and system that allows healthcare providers to monitor disabled, elderly or other high-risk individuals to prevent or reduce falls and/or mitigate the impact of a fall by delivering automated notification of "at risk" behavior and falls by such an individual. Two systems are used to identify patients—a skeletal tracking system that identifies patients by biometric indicators and a virtual blob detection system. In the virtual blob system, the monitored individual is virtually represented as a blob object of at least a specific size by a computerized monitoring system, and such system detects and alerts when the blob object enters or crosses into a virtually defined or designated blob detection zone and remains in the zone for at least a predetermined period of time. These systems may be used concurrently and conflicts between the systems may be resolved.

20 Claims, 19 Drawing Sheets

Related U.S. Application Data continuation of application No. 14/727,434, filed on Jun. 1, 2015, now Pat. No. 9,892,611.

(51) Int. Cl.

| | | |
|---|---|---|
| *G06T 7/20* | (2017.01) | |
| *G06K 9/32* | (2006.01) | |
| *G08B 23/00* | (2006.01) | |
| *A61B 5/11* | (2006.01) | |
| *G08B 25/14* | (2006.01) | |
| *G06K 9/44* | (2006.01) | |
| *G06T 7/246* | (2017.01) | |
| *G06F 3/00* | (2006.01) | |

(52) U.S. Cl.
CPC ..... *G06K 9/00369* (2013.01); *G06K 9/00771* (2013.01); *G06K 9/00778* (2013.01); *G06K 9/3241* (2013.01); *G06K 9/44* (2013.01); *G06T 7/20* (2013.01); *G06T 7/246* (2017.01); *G08B 23/00* (2013.01); *G08B 25/14* (2013.01); *H05K 999/99* (2013.01); *G06K 2009/3291* (2013.01); *G06T 2207/10021* (2013.01)

(58) Field of Classification Search
USPC .......................................................... 382/103
See application file for complete search history.

(56) References Cited

U.S. PATENT DOCUMENTS

| | | | |
|---|---|---|---|
| 5,031,228 A | 7/1991 | Lu | |
| 5,276,432 A | 1/1994 | Travis | |
| 5,448,221 A | 9/1995 | Weller | |
| 5,482,050 A | 1/1996 | Smokoff et al. | |
| 5,592,153 A | 1/1997 | Welling et al. | |
| 5,798,798 A | 8/1998 | Rector et al. | |
| 5,838,223 A | 11/1998 | Gallant et al. | |
| 5,915,379 A | 6/1999 | Wallace et al. | |
| 5,942,986 A | 8/1999 | Shabot et al. | |
| 6,050,940 A * | 4/2000 | Braun | G06F 19/3418 |
| | | | 600/300 |
| 6,095,984 A | 8/2000 | Amano et al. | |
| 6,160,478 A | 12/2000 | Jacobsen et al. | |
| 6,174,283 B1 | 1/2001 | Nevo et al. | |
| 6,188,407 B1 | 2/2001 | Smith et al. | |
| 6,269,812 B1 | 8/2001 | Wallace et al. | |
| 6,287,452 B1 * | 9/2001 | Allen | G01N 27/30 |
| | | | 204/291 |
| 6,322,502 B1 | 11/2001 | Schoenberg et al. | |
| 6,369,838 B1 | 4/2002 | Wallace et al. | |
| 6,429,869 B1 | 8/2002 | Kamakura et al. | |
| 6,614,349 B1 | 9/2003 | Proctor et al. | |
| 6,727,818 B1 | 4/2004 | Wildman et al. | |
| 6,804,656 B1 | 10/2004 | Rosenfeld et al. | |
| 7,015,816 B2 | 3/2006 | Wildman et al. | |
| 7,122,005 B2 | 10/2006 | Shusterman | |
| 7,154,397 B2 | 12/2006 | Zerhusen et al. | |
| 7,237,287 B2 | 7/2007 | Weismiller et al. | |
| 7,323,991 B1 | 1/2008 | Eckert et al. | |
| 7,408,470 B2 | 8/2008 | Wildman et al. | |
| 7,420,472 B2 | 9/2008 | Tran | |
| 7,430,608 B2 | 9/2008 | Noonan et al. | |
| 7,502,498 B2 | 3/2009 | Wen et al. | |
| 7,612,679 B1 | 11/2009 | Fackler et al. | |
| 7,669,263 B2 | 3/2010 | Menkedick et al. | |
| 7,715,387 B2 | 5/2010 | Schuman | |
| 7,724,147 B2 | 5/2010 | Brown | |
| 7,756,723 B2 | 7/2010 | Rosow et al. | |
| 7,890,349 B2 | 2/2011 | Cole et al. | |
| 7,895,055 B2 | 2/2011 | Schneider et al. | |
| 7,908,153 B2 | 3/2011 | Scherpbier et al. | |
| 7,945,457 B2 | 5/2011 | Zaleski | |
| 7,962,544 B2 | 6/2011 | Torok et al. | |
| 7,972,140 B2 | 7/2011 | Renaud | |
| 8,108,036 B2 | 1/2012 | Tran | |
| 8,123,685 B2 | 2/2012 | Brauers et al. | |
| 8,224,108 B2 | 7/2012 | Steinberg et al. | |
| 8,237,558 B2 | 8/2012 | Seyed Momen et al. | |
| 8,273,018 B1 | 9/2012 | Fackler et al. | |
| 8,432,263 B2 | 4/2013 | Kunz | |
| 8,451,314 B1 | 5/2013 | Cline et al. | |
| 8,529,448 B2 | 9/2013 | McNair | |
| 8,565,500 B2 | 10/2013 | Neff | |
| 8,620,682 B2 | 12/2013 | Bechtel et al. | |
| 8,655,680 B2 | 2/2014 | Bechtel et al. | |
| 8,700,423 B2 | 4/2014 | Eaton, Jr. et al. | |
| 8,727,981 B2 | 5/2014 | Bechtel et al. | |
| 8,769,153 B2 | 7/2014 | Dziubinski | |
| 8,890,937 B2 | 11/2014 | Skubic et al. | |
| 8,902,068 B2 | 12/2014 | Bechtel et al. | |
| 8,917,186 B1 | 12/2014 | Grant | |
| 8,953,886 B2 | 2/2015 | King et al. | |
| 9,072,929 B1 | 7/2015 | Rush et al. | |
| 9,129,506 B1 | 9/2015 | Kusens | |
| 9,147,334 B2 | 9/2015 | Long et al. | |
| 9,159,215 B1 | 10/2015 | Kusens | |
| 9,269,012 B2 | 2/2016 | Fotland | |
| 9,292,089 B1 | 3/2016 | Sadek | |
| 9,305,191 B2 | 4/2016 | Long et al. | |
| 9,408,561 B2 | 8/2016 | Stone et al. | |
| 9,489,820 B1 | 11/2016 | Kusens | |
| 9,519,969 B1 | 12/2016 | Kusens | |
| 9,524,443 B1 | 12/2016 | Kusens | |
| 9,536,310 B1 | 1/2017 | Kusens | |
| 9,538,158 B1 | 1/2017 | Rush et al. | |
| 9,563,955 B1 | 2/2017 | Kamarshi et al. | |
| 9,597,016 B2 | 3/2017 | Stone et al. | |
| 9,729,833 B1 | 8/2017 | Kusens | |
| 9,741,227 B1 | 8/2017 | Kusens | |
| 9,892,310 B2 | 2/2018 | Kusens et al. | |
| 9,892,311 B2 | 2/2018 | Kusens et al. | |
| 9,892,611 B1 | 2/2018 | Kusens | |
| 9,905,113 B2 | 2/2018 | Kusens | |
| 10,055,961 B1 | 8/2018 | Johnson et al. | |
| 10,096,223 B1 | 10/2018 | Kusens | |
| 10,210,378 B2 | 2/2019 | Kusens et al. | |
| 10,225,522 B1 | 3/2019 | Kusens | |
| 10,276,019 B2 | 4/2019 | Johnson et al. | |
| 2002/0015034 A1 | 2/2002 | Malmborg | |
| 2002/0077863 A1 | 6/2002 | Rutledge et al. | |
| 2002/0101349 A1 | 8/2002 | Rojas, Jr. | |
| 2002/0115905 A1 | 8/2002 | August | |
| 2002/0183976 A1 | 12/2002 | Pearce | |
| 2003/0037786 A1 | 2/2003 | Biondi et al. | |
| 2003/0070177 A1 | 4/2003 | Kondo et al. | |
| 2003/0092974 A1 | 5/2003 | Santos et al. | |
| 2003/0095147 A1 | 5/2003 | Daw | |
| 2003/0135390 A1 | 7/2003 | O'brien et al. | |
| 2003/0140928 A1 | 7/2003 | Bui et al. | |
| 2003/0227386 A1 | 12/2003 | Pulkkinen et al. | |
| 2004/0019900 A1 | 1/2004 | Knightbridge et al. | |
| 2004/0052418 A1 | 3/2004 | Delean | |
| 2004/0054760 A1 | 3/2004 | Ewing et al. | |
| 2004/0097227 A1 | 5/2004 | Siegel | |
| 2004/0116804 A1 | 6/2004 | Mostafavi | |
| 2004/0193449 A1 | 9/2004 | Wildman et al. | |
| 2005/0038326 A1 | 2/2005 | Mathur | |
| 2005/0182305 A1 | 8/2005 | Hendrich | |
| 2005/0231341 A1 | 10/2005 | Shimizu | |
| 2005/0249139 A1 | 11/2005 | Nesbit | |
| 2006/0004606 A1 | 1/2006 | Wendl et al. | |
| 2006/0047538 A1 | 3/2006 | Condurso et al. | |
| 2006/0049936 A1 | 3/2006 | Collins et al. | |
| 2006/0058587 A1 | 3/2006 | Heimbrock et al. | |
| 2006/0089541 A1 | 4/2006 | Braun et al. | |
| 2006/0092043 A1 | 5/2006 | Lagassey | |
| 2006/0107295 A1 | 5/2006 | Margis et al. | |
| 2006/0145874 A1 | 7/2006 | Fredriksson et al. | |
| 2006/0261974 A1 | 11/2006 | Albert et al. | |
| 2007/0085690 A1 | 4/2007 | Tran | |
| 2007/0118054 A1 | 5/2007 | Pinhas et al. | |
| 2007/0120689 A1 | 5/2007 | Zerhusen et al. | |
| 2007/0129983 A1 | 6/2007 | Scherpbier et al. | |

(56) References Cited

U.S. PATENT DOCUMENTS

| | | |
|---|---|---|
| 2007/0136218 A1 | 6/2007 | Bauer et al. |
| 2007/0159332 A1 | 7/2007 | Koblasz |
| 2007/0279219 A1 | 12/2007 | Warriner |
| 2007/0296600 A1 | 12/2007 | Dixon et al. |
| 2008/0001735 A1 | 1/2008 | Tran |
| 2008/0001763 A1 | 1/2008 | Raja et al. |
| 2008/0002860 A1 | 1/2008 | Super et al. |
| 2008/0004904 A1 | 1/2008 | Tran |
| 2008/0009686 A1 | 1/2008 | Hendrich |
| 2008/0015903 A1 | 1/2008 | Rodgers |
| 2008/0021731 A1 | 1/2008 | Rodgers |
| 2008/0071210 A1 | 3/2008 | Moubayed et al. |
| 2008/0087719 A1 | 4/2008 | Sahud |
| 2008/0106374 A1 | 5/2008 | Sharbaugh |
| 2008/0126132 A1 | 5/2008 | Warner et al. |
| 2008/0228045 A1 | 9/2008 | Gao et al. |
| 2008/0249376 A1 | 10/2008 | Zaleski |
| 2008/0267447 A1 | 10/2008 | Kelusky et al. |
| 2008/0277486 A1 | 11/2008 | Seem et al. |
| 2008/0281638 A1 | 11/2008 | Weatherly et al. |
| 2009/0082829 A1 | 3/2009 | Panken et al. |
| 2009/0091458 A1 | 4/2009 | Deutsch |
| 2009/0099480 A1 | 4/2009 | Salgo et al. |
| 2009/0112630 A1 | 4/2009 | Collins et al. |
| 2009/0119843 A1 | 5/2009 | Rodgers et al. |
| 2009/0177327 A1 | 7/2009 | Turner et al. |
| 2009/0224924 A1 | 9/2009 | Thorp |
| 2009/0278934 A1 | 11/2009 | Ecker et al. |
| 2009/0322513 A1 | 12/2009 | Hwang et al. |
| 2010/0117836 A1 | 5/2010 | Seyed momen et al. |
| 2010/0169114 A1 | 7/2010 | Henderson et al. |
| 2010/0169120 A1 | 7/2010 | Herbst et al. |
| 2010/0172567 A1 | 7/2010 | Prokoski |
| 2010/0176952 A1 | 7/2010 | Bajcsy et al. |
| 2010/0188228 A1 | 7/2010 | Hyland |
| 2010/0205771 A1 | 8/2010 | Pietryga et al. |
| 2010/0245577 A1 | 9/2010 | Yamamoto et al. |
| 2010/0285771 A1 | 11/2010 | Peabody |
| 2010/0305466 A1 | 12/2010 | Corn |
| 2011/0018709 A1 | 1/2011 | Kornbluh |
| 2011/0022981 A1 | 1/2011 | Mahajan et al. |
| 2011/0025493 A1 | 2/2011 | Papadopoulos et al. |
| 2011/0025499 A1 | 2/2011 | Hoy et al. |
| 2011/0035057 A1 | 2/2011 | Receveur et al. |
| 2011/0035466 A1 | 2/2011 | Panigrahi |
| 2011/0054936 A1 | 3/2011 | Cowan et al. |
| 2011/0068930 A1 | 3/2011 | Wildman et al. |
| 2011/0077965 A1 | 3/2011 | Nolte et al. |
| 2011/0087079 A1 | 4/2011 | Aarts |
| 2011/0102133 A1 | 5/2011 | Shaffer |
| 2011/0102181 A1 | 5/2011 | Metz et al. |
| 2011/0106560 A1 | 5/2011 | Eaton et al. |
| 2011/0106561 A1 | 5/2011 | Eaton et al. |
| 2011/0175809 A1 | 7/2011 | Markovic et al. |
| 2011/0190593 A1 | 8/2011 | Mcnair |
| 2011/0227740 A1 | 9/2011 | Wohltjen |
| 2011/0245707 A1 | 10/2011 | Castle et al. |
| 2011/0254682 A1 | 10/2011 | Sigrist Christensen |
| 2011/0288811 A1 | 11/2011 | Greene |
| 2011/0295621 A1 | 12/2011 | Farooq et al. |
| 2011/0301440 A1 | 12/2011 | Riley et al. |
| 2011/0313325 A1 | 12/2011 | Cuddihy |
| 2012/0025991 A1 | 2/2012 | O'keefe et al. |
| 2012/0026308 A1 | 2/2012 | Johnson et al. |
| 2012/0075464 A1 | 3/2012 | Derenne et al. |
| 2012/0092162 A1 | 4/2012 | Rosenberg |
| 2012/0098918 A1 | 4/2012 | Murphy |
| 2012/0140068 A1 | 6/2012 | Monroe et al. |
| 2012/0154582 A1 | 6/2012 | Johnson et al. |
| 2012/0212582 A1 | 8/2012 | Deutsch |
| 2012/0259650 A1 | 10/2012 | Mallon et al. |
| 2012/0314901 A1 | 12/2012 | Hanson et al. |
| 2013/0027199 A1 | 1/2013 | Bonner |
| 2013/0028570 A1 | 1/2013 | Suematsu et al. |
| 2013/0120120 A1 | 5/2013 | Long et al. |
| 2013/0122807 A1 | 5/2013 | Tenarvitz et al. |
| 2013/0184592 A1 | 7/2013 | Venetianer et al. |
| 2013/0265482 A1 | 10/2013 | Funamoto |
| 2013/0309128 A1 | 11/2013 | Voegeli et al. |
| 2013/0332184 A1 | 12/2013 | Burnham et al. |
| 2014/0039351 A1 | 2/2014 | Mix et al. |
| 2014/0070950 A1 | 3/2014 | Snodgrass |
| 2014/0085501 A1 | 3/2014 | Tran |
| 2014/0086450 A1 | 3/2014 | Huang et al. |
| 2014/0155755 A1 | 6/2014 | Pinter et al. |
| 2014/0191861 A1 | 7/2014 | Scherrer |
| 2014/0267625 A1 | 9/2014 | Clark et al. |
| 2014/0267736 A1 | 9/2014 | Delean |
| 2014/0327545 A1 | 11/2014 | Bolling et al. |
| 2014/0328512 A1 | 11/2014 | Gurwicz et al. |
| 2014/0333744 A1 | 11/2014 | Baym et al. |
| 2014/0333776 A1 | 11/2014 | Dedeoglu et al. |
| 2014/0354436 A1 | 12/2014 | Nix et al. |
| 2014/0365242 A1 | 12/2014 | Neff |
| 2015/0109442 A1 | 4/2015 | Derenne et al. |
| 2015/0206415 A1 | 7/2015 | Wegelin et al. |
| 2015/0269318 A1 | 9/2015 | Neff |
| 2015/0278456 A1 | 10/2015 | Bermudez rodriguez et al. |
| 2015/0294143 A1 | 10/2015 | Wells et al. |
| 2016/0022218 A1 | 1/2016 | Hayes et al. |
| 2016/0070869 A1 | 3/2016 | Portnoy |
| 2016/0093195 A1 | 3/2016 | Ophardt |
| 2016/0127641 A1 | 5/2016 | Gove |
| 2016/0217347 A1 | 7/2016 | Mineo |
| 2016/0253802 A1 | 9/2016 | Venetianer et al. |
| 2016/0267327 A1 | 9/2016 | Franz et al. |
| 2016/0360970 A1 | 12/2016 | Tzvieli et al. |
| 2017/0055917 A1 | 3/2017 | Stone et al. |
| 2017/0143240 A1 | 5/2017 | Stone et al. |
| 2017/0337682 A1 | 11/2017 | Liao et al. |
| 2018/0018864 A1 | 1/2018 | Baker |
| 2018/0068545 A1 | 3/2018 | Kusens |
| 2018/0357875 A1 | 12/2018 | Kusens |
| 2019/0006046 A1 | 1/2019 | Kusens et al. |
| 2019/0029528 A1 | 1/2019 | Tzvieli et al. |
| 2019/0043192 A1 | 2/2019 | Kusens et al. |
| 2019/0122028 A1 | 4/2019 | Kusens et al. |
| 2019/0205630 A1 | 7/2019 | Kusens |
| 2019/0206218 A1 | 7/2019 | Kusens et al. |

OTHER PUBLICATIONS

Notice of Allowance received for U.S. Appl. No. 16/380,013, dated Jul. 10, 2019, 10 pages.

Final Office Action received for U.S. Appl. No. 13/543,816, dated Jun. 17, 2014, 15 pages.

Final Office Action received for U.S. Appl. No. 14/084,588, dated Dec. 19, 2014, 24 pages.

Final Office Action received for U.S. Appl. No. 14/575,850, dated Dec. 12, 2017, 10 pages.

Final Office Action received for U.S. Appl. No. 14/599,498, dated Oct. 12, 2017, 28 pages.

Final Office Action received for U.S. Appl. No. 14/611,363, dated Apr. 28, 2017, 20 pages.

Final Office Action received for U.S. Appl. No. 14/623,349, dated Oct. 4, 2017, 29 pages.

Final Office Action received for U.S. Appl. No. 14/724,969, dated Jul. 28, 2016, 26 pages.

Final Office Action received for U.S. Appl. No. 14/757,877, dated Sep. 29, 2017, 22 pages.

Final Office Action received for U.S. Appl. No. 15/134,189, dated Jul. 12, 2018, 23 pages.

Final Office Action received for U.S. Appl. No. 15/285,416, dated Aug. 23, 2017, 16 pages.

Final Office Action received for U.S. Appl. No. 15/285,416, dated Jul. 5, 2018, 8 pages.

Final Office Action received for U.S. Appl. No. 15/396,263, dated Oct. 18, 2017, 20 pages.

First Action Interview Office Action received for U.S. Appl. No. 14/244,160, dated Nov. 28, 2017, 5 pages.

(56) References Cited

OTHER PUBLICATIONS

Kusens, Neil, Unpublished U.S. Appl. No. 14/613,866, filed Feb 4, 2015, titled "Method and System for Determining Whether an Individual Takes Appropriate Measures to Prevent the Spread of Healthcare Associated Infections Along With Centralized Monitoring".
Kusens, Neil, Unpublished U.S. Appl. No. 14/084,588, filed Nov. 19, 2013, titled "Method for Determining Whether an Individual Leaves a Prescribed Virtual Perimeter".
Kusens, Neil, Unpublished U.S. Appl. No. 14/575,850, filed Dec. 18, 2014, titled "Method and Process for Determining Whether an Individual Suffers a Fall Requiring Assistance".
Kusens, Neil, Unpublished U.S. Appl. No. 14/599,498, filed Jan. 17, 2015, titled "Method and System for Determining Whether an Individual Takes Appropriate Measures to Prevent the D Spread of Healthcare Associated Infections".
Kusens, Neil, Unpublished U.S. Appl. No. 14/611,363, filed Feb. 2, 2015, titled "Method and System for Determining Whether an Individual Takes Appropriate Measures to Prevent the Spread of Healthcare Associated Infections".
Kusens, Neil, Unpublished U.S. Appl. No. 14/623,349, filed Feb. 16, 2015, titled "Method for Determining Whether an Individual Enters a Prescribed Virtual Zone Using 3D Blob Detection".
Kusens, Neil, Unpublished U.S. Appl. No. 13/543,816, filed Jul. 7, 2012, titled "Method and Process for Determining Whether an Individual Suffers a Fall Requiring Assistance".
Kusens, Neil, Unpublished U.S. Appl. No. 14/724,969, filed May 29, 2015, titled "Method and Process for Determining Whether an Individual Suffers a Fall Requiring Assistance".
Kusens, Neil, Unpublished U.S. Appl. No. 14/727,434, filed Jun. 1, 2015, titled "Method for Determining Whether Enters a Prescribed Virtual Zone Using Skeletal Tracking and 3D Blob Detection".
Kusens, Neil, Unpublished U.S. Appl. No. 14/728,762, filed Jun. 2, 2015, titled "Method for Determining Whether an Individual Leaves a Prescribed Virtual Perimeter".
Kusens, Neil, Unpublished U.S. Appl. No. 14/743,264, filed Jun. 18, 2015, titled "System for Determining Whether an Individual Enters a Prescribed Virtual Zone Using 3D Blob Detection".
Kusens, Neil, Unpublished U.S. Appl. No. 14/743,447, filed Jun. 18, 2015, titled "System for Determining Whether an Individual Suffers a Fall Requiring Assistance".
Kusens, Neil, Unpublished U.S. Appl. No. 14/743,499, filed Jun. 18, 2015, titled "System for Determining Whether an Individual Suffers a Fall Requiring Assistance".
Mooney, Tom, Rhode Island ER First to Test Google Glass on Medical Conditions, retrived from <https://www.ems1.com/ems-products/technology/articles/1860487-Rhode-Island-ER-first-to-test-Google-Glass-on-medical-conditions/>, Mar. 11, 2014, 3 pages.
Non-Final Office Action received for U.S. Appl. No. 15/148,151, dated May 8, 2018, 5 pages.
Non-Final Office Action received for U.S. Appl. No. 15/285,416, dated Apr. 11, 2017, 13 pages.
Non-Final Office Action received for U.S. Appl. No. 15/285,416, dated Mar. 12, 2018, 20 pages.
Non-Final Office Action received for U.S. Appl. No. 15/395,250, dated May 8, 2017, 19 pages.
Non-Final Office Action received for U.S. Appl. No. 15/395,526, dated Apr. 27, 2017, 16 pages.
Non-Final Office Action received for U.S. Appl. No. 15/395,762, dated May 31, 2018, 24 pages.
Non-Final Office Action received for U.S. Appl. No. 15/396,263, dated Apr. 14, 2017, 18 pages.
Non-Final Office Action received for U.S. Appl. No. 15/628,318, dated Jun. 8, 2018, 9 pages.
Non-Final Office Action received for U.S. Appl. No. 15/728,110, dated May 2, 2018, 8 pages.
Non-Final Office Action received for U.S. Appl. No. 15/848,621, dated May 31, 2018, 23 pages.
Non-Final Office Action received for U.S. Appl. No. 13/543,816, dated Dec. 30, 2013, 9 pages.
Non-Final Office Action received for U.S. Appl. No. 13/543,816, dated Dec. 1, 2014, 18 pages.
Non-Final Office Action received for U.S. Appl. No. 14/084,588, dated Jul. 16, 2014, 12 pages.
Non-Final Office Action received for U.S. Appl. No. 14/339,397, dated Oct. 7, 2015, 16 pages.
Non-Final Office Action received for U.S. Appl. No. 14/575,850, dated Mar. 11, 2016, 10 pages.
Non-Final Office Action received for U.S. Appl. No. 14/599,498, dated May 31, 2017, 24 pages.
Non-Final Office Action received for U.S. Appl. No. 14/611,363, dated Jan. 11, 2017, 19 pages.
Non-Final Office Action received for U.S. Appl. No. 14/611,363, dated May 7, 2018, 6 pages.
Non-Final Office Action received for U.S. Appl. No. 14/623,349, dated Apr. 5, 2017, 15 pages.
Non-Final Office Action received for U.S. Appl. No. 14/724,969, dated Feb. 11, 2016, 14 pages.
Non-Final Office Action received for U.S. Appl. No. 14/727,434, dated Sep. 23, 2016, 9 pages.
Non-Final Office Action received for U.S. Appl. No. 14/743,499, dated May 23, 2016, 6 pages.
Non-Final Office Action received for U.S. Appl. No. 14/757,593, dated Apr. 21, 2017, 9 pages.
Non Final Office Action received for U.S. Appl. No. 15/395,243, dated Feb. 14, 2019, 14 pages.
Non Final Office Action received for U.S. Appl. No. 16/216,210, dated Feb. 13, 2019, 29 pages.
Non Final Office Action received for U.S. Appl. No. 16/107,567, dated Mar. 29, 2019, 8 pages.
Non-Final Office Action received for U.S. Appl. No. 15/395,762, dated May 1, 2019, 27 pages.
Non-Final Office Action received for U.S. Appl. No. 15/856,419, dated May 2, 2019, 8 pages.
Conaire, et al., "Fusion of Infrared and Visible Spectrum Video for Indoor Surveillance", WIAMIS, Apr. 2005, 4 pages.
Final Office Action received for U.S. Appl. No. 15/395,243, dated Jun. 11, 2019, 18 pages.
Non-Final Office Action received for U.S. Appl. No. 15/134,189, dated May 9, 2019, 30 pages.
Preinterview First Office Action received for U.S. Appl. No. 15/857,696, dated May 23, 2019, 14 pages.
Non-Final Office Action received for U.S. Appl. No. 14/757,593, dated Aug. 16, 2017, 8 pages.
Non-Final Office Action received for U.S. Appl. No. 14/757,877, dated Feb. 23, 2017, 24 pages.
Notice of Allowance received for U.S. Appl. No. 13/543,816, dated Jun. 5, 2015, 5 pages.
Notice of Allowance received for U.S. Appl. No. 14/575,850, dated Jun. 13, 2018, 5 pages.
Notice of Allowance received for U.S. Appl. No. 14/599,498, dated Jul. 18, 2018, 6 pages.
Notice of Allowance received for U.S. Appl. No. 14/611,363, dated Dec. 29, 2017, 11 pages.
Notice of Allowance received for U.S. Appl. No. 14/613,866, dated Mar. 20, 2017, 11 pages.
Notice of Allowance received for U.S. Appl. No. 14/623,349, dated Jun. 18, 2018, 11 pages.
Notice of Allowance received for U.S. Appl. No. 14/724,969, dated Apr. 21, 2017, 8 pages.
Notice of Allowance received for U.S. Appl. No. 14/724,969, dated Dec. 23, 2016, 5 pages.
Notice of Allowance received for U.S. Appl. No. 14/127,434, dated Apr. 25, 2017, 9 pages.
Notice of Allowance received for U.S. Appl. No. 14/727,434, dated Jan. 4, 2018, 2 pages.
Notice of Allowance received for U.S. Appl. No. 14/727,434, dated Jul. 5, 2017, 9 pages.
Notice of Allowance received for U.S. Appl. No. 14/727,434, dated Oct. 10, 2017, 9 pages.
Notice of Allowance received for U.S. Appl. No. 14/728,762, dated Jun. 27, 2016, 14 pages.

(56) References Cited

OTHER PUBLICATIONS

Notice of Allowance received for U.S. Appl. No. 14/743,264, dated Jul. 18, 2016, 16 pages.
Notice of Allowance received for U.S. Appl. No. 14/743,264, dated Nov. 9, 2016, 14 pages.
Notice of Allowance received for U.S. Appl. No. 14/743,264, dated Oct. 14, 2016, 14 pages.
Notice of Allowance received for U.S. Appl. No. 14/743,447, dated Aug. 26, 2016, 5 pages.
Notice of Allowance received for U.S. Appl. No. 14/743,447, dated Jun. 22, 2016, 4 pages.
Notice of Allowance received for U.S. Appl. No. 14/743,447, dated May 31, 2016, 8 pages.
Notice of Allowance received for U.S. Appl. No. 14/743,447, dated Nov. 14, 2016, 5 pages.
Notice of Allowance received for U.S. Appl. No. 14/743,499, dated Sep. 19, 2016, 5 pages.
Notice of Allowance received for U.S. Appl. No. 14/757,593, dated Jun. 4, 2018, 5 pages.
Notice of Allowance received for U.S. Appl. No. 15/279,054, dated Nov. 27, 2017, 2 pages.
Notice of Allowance received for U.S. Appl. No. 15/279,054, dated Oct. 20, 2017, 13 pages.
Notice of Allowance received for U.S. Appl. No. 15/395,250, dated Sep. 26, 2017, 13 pages.
Notice of Allowance received for U.S. Appl. No. 15/395,526, dated Sep. 21, 2017, 13 pages.
Notice of Allowance received for U.S. Appl. No. 15/395,716, dated Apr. 19, 2017, 5 pages.
Notice of Allowance received for U.S. Appl. No. 15/395,716, dated Dec. 6, 2017, 5 pages.
Notice of Allowance received for U.S. Appl. No. 15/395,716, dated May 9, 2018, 5 pages.
Notice of Allowance received for U.S. Appl. No. 15/396,263, dated Jul. 13, 2018, 9 pages.
Notice of Allowance received for U.S. Appl. No. 15/728,110, dated Jul. 23, 2018, 15 pages.
Notice of Allowance received for U.S. Appl. No. 15/728,110, dated Sep. 21, 2018, 2 pages.
Notice of Allowance received for U.S. Appl. No. 15/395,716, dated Jun. 19, 2018, 2 pages.
Notice of Allowance received for U.S. Appl. No. 15/395,716, dated Jul. 24, 2017, 5 pages.
Pre-interview First Office Action received for U.S. Appl. No. 15/910,645, dated May 21, 2018, 14 pages.
Pre-interview First Office Action received for U.S. Appl. No. 15/395,716, dated Feb. 24, 2017, 5 pages.
Pre-interview First Office Action received for U.S. Appl. No. 15/134,189, dated Nov. 22, 2017, 5 pages.
Raheja, et al., Human Facial Expression Detection From Detected in Captured Image Using Back Propagation Neural Network, International Journal of Computer Science and Information Technology (IJCSIT), vol. 2, No. 1, Feb. 2010, 7 pages.
Virtual Patient Observation: Centralize Monitoring of High-Risk Patients with Video—Cisco Video Surveillance Manager, Retrived from <https://www.cisco.com/c/en/us/products/collateral/physical-security/video-surveillance-manager/whitepaper_11-715263.pdf>.

\* cited by examiner

Figure 7

- Virtual Blob Detection Zone(s)
- Bed Zone
- Auto Bed Zone (Select Patient)
- Auto Bed Zone (Auto-select)
- Saved Zones
- Clear All
- Rails (Trip Wires)

SYSTEMS AND METHODS FOR DETERMINING WHETHER AN INDIVIDUAL ENTERS A PRESCRIBED VIRTUAL ZONE USING SKELETAL TRACKING AND 3D BLOB DETECTION

CROSS-REFERENCE TO RELATED APPLICATIONS

This application, having 16/166,857 and entitled "Systems and Methods for Determining Whether an Individual Enters a Prescribed Virtual Zone Using Skeletal Tracking and 3D Blob Detection" is a continuation of pending U.S. application Ser. No. 15/728,110 filed Oct. 9, 2017, and entitled "Method for Determining Whether an Individual Enters a Prescribed Virtual Zone Using Skeletal Tracking and 3D Blob Detection," which is a continuation of U.S. application Ser. No. 14/727,434, filed Jun. 1, 2015, now U.S. Pat. No. 9,892,611, issued Feb. 13, 2018, the entirety of each of which is incorporated by reference herein.

FIELD OF THE DISCLOSURE

The present disclosure is generally directed to patient monitoring systems and particularly to a system and method for monitoring patients in a manner which prevents or reduces patient falls.

BACKGROUND

According to recent studies, falls are a leading cause of death among people over the age of 65 years, and 10% of the fatal falls for patients over 65 years of age occur in a hospital setting. For the general population, studies estimate that patient falls occur in 1.9 to 3% of all acute care hospitalizations. Of these hospital-based falls, approximately 30% will result in a serious injury with the cost to care for these injuries estimated to reach $54.9 billion per year by 2020. Current technologies that exist to assist in the prevention of falls are limited in their capabilities. These include pressure pads on the bed that trigger an alert when no pressure is detected on the pad, pressure pads on the floor and light beams that create a perimeter with alarms going off upon interruption of the beam. The pressure pads are ineffective as they do not prevent the fall but, rather, alert after the fact when it is too late. Additionally they are prone to false positive alerts. The light beams are also prone to false alerts when the patient or visitor simply reaches through it or the caregiver breaks the beam while delivering medication, food, or drink or conducting a procedure on the patient. The present disclosure is directed to addressing these above-described shortcomings with current technology.

SUMMARY OF THE DISCLOSURE

Generally disclosed is a novel method and system that allows healthcare providers, hospitals, skilled nursing facilities, and other persons to monitor disabled, elderly, or other high-risk individuals and utilize the described technology to prevent or reduce falls and/or mitigate the impact of a fall by delivering automated notification of "at risk" behavior and/or falls by such an individual being monitored, especially falls and/or behavior where assistance is required, using a skeletal tracking system and a virtual blob detection system.

With skeletal tracking alone, there can be factors affecting the cameras/image-video quality which affects the ability of the detection/monitoring system to detect a skeleton. Such factors, especially in a hospital, include, but are not limited to, sheets/blankets covering a patient, trays positioned over the bed hiding the patient, and the patient blending into the bed and not having a skeleton recognized.

With blob detection alone, there can be an increase in false positives in detecting falls and "at risk" behavior. These false positives can occur because blob detection does not differentiate between types of 3D objects. Blankets, trays, caretakers, or other 3D objects can trigger an automated notification. Blob recognition also does not differentiate between parts of the body.

The present disclosure using of a skeletal tracking system with a virtual blob detection system addresses or at least reduces the shortcomings of both systems. Skeletal tracking can be used to reduce or eliminate false positives generated by a virtual blob detection system. Virtual blob detection relies on 3D object detection, which works regardless of how much of the person is viewable by the camera or whether other objects are blocking the view of the camera. Even in poor lighting conditions, both the virtual blob detection system and skeletal tracking system can still capture and/or recognize movement as the system can use an IR Depth Map to perform the blob and/or skeletal detection, which does not rely on lighting conditions.

The present disclosure uses both a skeletal tracking system and a virtual blob detection system to track whether an individual has fallen or engaged in "at risk" behavior. When the skeletal tracking system is unable to track a skeleton, then a virtual blob detection system is used to capture and/or recognize movement. In the alternative, both a skeletal tracking system and a blob detection system can monitor an individual simultaneously, and a notification is delivered when either system detects a fall or "at risk" behavior.

The following non-limiting definitions are provided as aid in understanding the disclosed novel method and system:

| | |
|---|---|
| 3D Camera, Motion and Sound sensor | An electronic device that contains one or more cameras capable of identifying individual objects, people, and motion regardless of lighting conditions as well as one or more microphones to detect audio. The cameras can utilize technologies including but not limited to color RGB, CMOS sensors, infrared projectors and RF-modulated light. They may also contain microprocessors and image sensors to detect and process information both sent out and received by the various cameras. The electronic device calculates if there has been a change in location of the person or object of interest over a period of time. As a non-limiting example, an object can be, at time T1, located at coordinates (x1, y1, z1) in a picture frame taken by the camera. At time T2, the object is captured by the picture frame taken by the camera at coordinates (x2, y2, z2). Based on this information, motion, speed, and direction can be derived utilizing the elapsed time and comparing the two 3D coordinates over the elapsed time. As opposed to conventional motion sensors, which use captured motion to control a camera, the 3D camera, motion, and sound | sensors used in accordance with the present disclosure uses the a camera in order to compute the motion as well as the size of the object. The camera/sensors are preferably continuously on at all times during while the monitoring is occurring, regardless of whether the person or object of interest is moving or not. The object size (minimum and/or maximum) can be configured through the software within, running, operating and/or controlling the computerized virtual blob detection monitoring system. A 3D camera, motion, and sound sensor can additionally be programmed to lock on a person and can send back to the computerized monitoring system the 3D coordinates of the joints in the person's body and a skeletal outline of the person. As a non-limiting example, a person's right arm can be, at time T1, located at coordinates (x1, y1, z1) in a picture frame taken by the camera. At time T2, the right arm is captured by the picture frame taken by the camera at coordinates (x2, y2, z2). Based on this information, motion, speed and direction can be derived utilizing the elapsed time and comparing the two 3D coordinates over the elapsed time. The camera preferably views the entire bed of a patient or a large portion of the bed or other area that the patient is resting at (i.e. chair, couch, etc.) simply by its placement in a manner sufficient for the monitored area to be visible to the camera. Thus, the camera does not require any triggering event to cause the camera to begin recording video and/or 3D depth data or transmitting video and/or 3D depth data to the other components of the system for analysis. Because the video camera may be recording or otherwise transmitting video and/or 3D depth data to the other system components at all times during monitoring, the electronic device is able to immediately track, capture and/or record the monitored individual's movements at all times within the room or monitored area and will be able to provide information as to whether and when the individual begins to move or begins to get up to move. Preferably the 3D camera, motion, and sound sensor record, capture, and/or stream video and/or 3D depth data. As video is technically made up of individual picture frames (i.e. 30 frames per second of video), the above reference to picture frames is referring to frames of video.

Whether used with skeletal tracking or virtual blob detection, depth sensitivity comes into play with both methods in order to minimize false alarms, as objects behind and in front of the patient can be effectively ignored. The preferred use of depth as a factor also differentiates the current monitoring system from motion/object detection systems that rely on 2D images.

The 3D camera, motion, and sound sensor can be located within the room of the patient being monitored and/or potentially just outside of the patient's room. It is connected to the computerized communication and computerized monitoring systems via a data connection (TCP/IP or comparable technology).

| | |
|---|---|
| Computerized Virtual Blob Detection Monitoring System | A computer system specifically designed and programmed to create virtual blob detection zones around a specific object, including but not limited to a hospital bed, and that monitors activity based on information received from the 3D camera, motion, and sound sensor. The computerized monitoring system will preferably be located within the patient's room and can be connected to the centralized monitoring station at the facility but can also be located at any physical location so long as a data connection (TCP/IP or comparable technology) exists between the computerized virtual blob detection monitoring system, the computerized communication system, the centralized monitoring station, and the 3D camera, motion, and sound sensor. |
| Computerized Communication System | A computer system specifically designed and programmed to facilitate communication between the monitored patient and the computerized monitoring system in the event of either an object, meeting the preprogrammed or preconfigured size for a triggering object, enters the virtual blob detection zone or the computerized skeletal tracking system determines the patient has fallen or performed an "at risk" behavior. This system may include but is not limited to amplified speakers, microphones, lights, monitors, computer terminals, mobile phones and/or other technologies to allow for the electronic communication to take place. The computerized communication system will preferably be located within the room of the patient being monitored, but certain components of the system are mobile by their nature (i.e. mobile phones, pagers, computers) and can also be located at any location so long as a data connection (TCP/IP or comparable technology) exists between the computerized monitoring system, the computerized communication system, the centralized monitoring station and 3D camera, motion, and sound sensor. |
| Computerized Skeletal Tracking System | A computer system specifically designed and programmed to lock onto an individual and send the 3D coordinates of the joints in an individual's body and a skeletal outline of the individual based on information received from the 3D camera, motion, and sound sensor. The computerized skeletal tracking system will preferably be located within the patient's room and can be connected to the centralized monitoring station at the facility but can also be located at any physical location so |

| | -continued |
|---|---|
| | long as a data connection (TCP/IP or comparable technology) exists between the computerized skeletal tracking system, the computerized communication system, the centralized monitoring station and the 3D camera, motion, and sound sensor. |
| System Database | A computer database that stores records, documents, or other files of all alerts generated, notifications, confirmation requests, responses, and reconfirmation requests, or any other desired information concerning a triggering event or lack of a triggering event. |
| Centralized Monitoring Primary Display | A computer display connected to the centralized monitoring station, providing video and audio of all patient rooms connected to the centralized monitoring station. |
| Centralized Monitoring Alert Display | A computer display connected to the centralized monitoring station, providing video and audio of any patient room where an object (such as an individual) is deemed to have entered a virtual blob detection zone, fallen, or performed an "at risk" behavior, preferably at the moment such determination is made. |
| Caregiver | A relative, friend, individual, company or facility whose purpose is to provide assistance in daily living activities for individuals who are disabled, elderly or otherwise in needs of assistance. |

BRIEF DESCRIPTION OF THE DRAWINGS

FIGS. 5 through 17 illustrate various screen shots for configuring the system for operation, including defining a bed zone, virtual blob detection zone(s), and alert types in accordance with an embodiment of the present disclosure;

DETAILED DESCRIPTION

Figure 1:
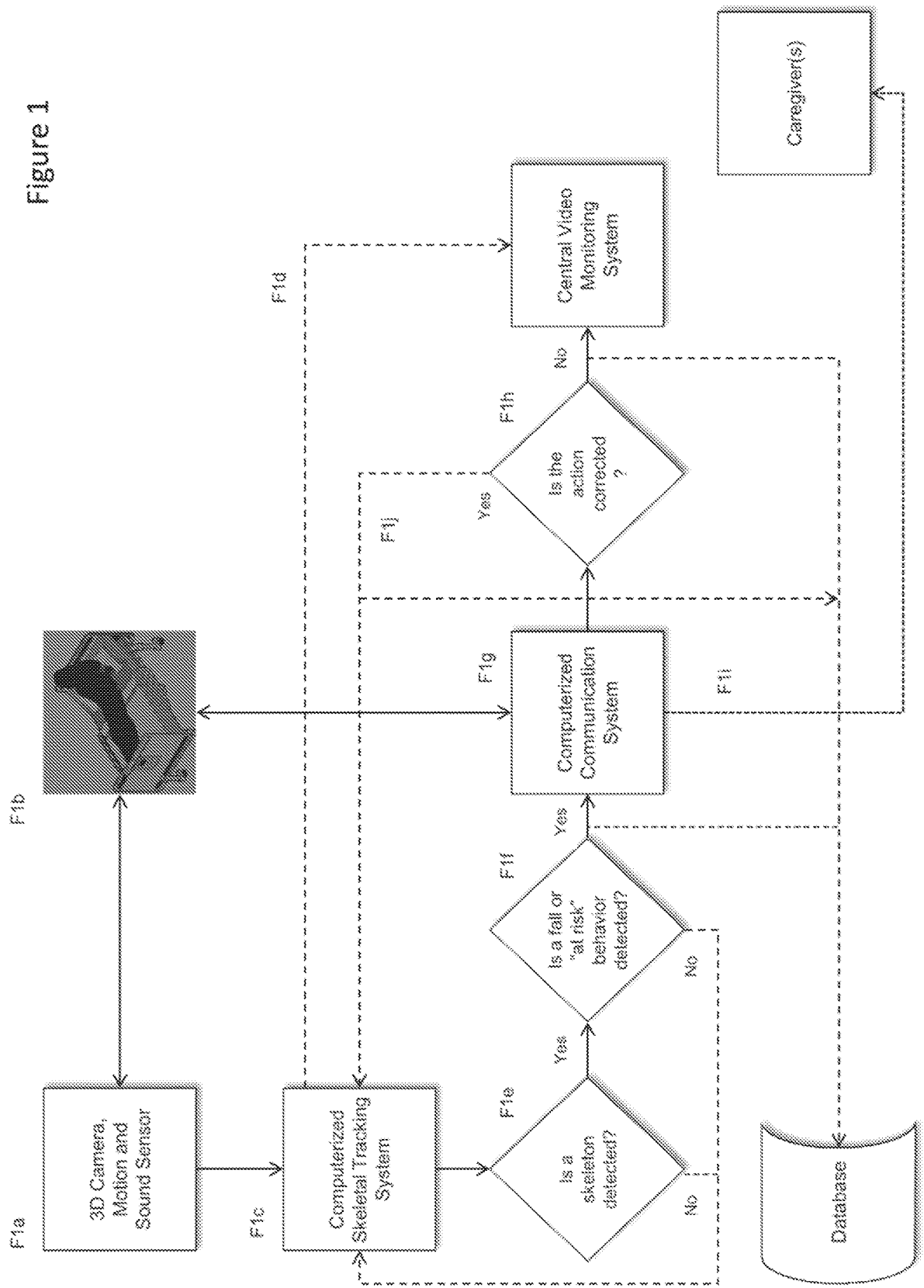
FIG. 1 is a block diagram of a computerized skeletal tracking, monitoring and alerting system and method in accordance with an embodiment of the present invention.

FIG. 1 illustrates a block diagram for the computerized skeletal tracking configuration, monitoring, and alerting system and a method of the disclosed system. Specifically, FIG. 1 shows the workflow for monitoring an individual's status through the use of one or more 3D camera, motion, and sound sensors.

At step F1a, one or more 3D camera, motion and/or sound sensors can be installed in the patient's or individual's room. At step F1b, the one or more 3D camera, motion and/or sound sensors can be configured to recognize the patient or monitored individual using biometric identifiers such as facial recognition, height, distance between points on the body, etc. The patient's body can be recognized and tracked as one or more skeletal components. Alternatively, the patient can be identified by means of a user creating a three-dimensional zone around the patient through a software application stored on a computerized skeletal tracking system or through the use of an electronic transmitter on the patient's or other individual's person. Once a patient is identified, the software can automatically generate or allow the user to generate a configurable three-dimensional zone or perimeter around the patient and/or the patient's bed that acts as a virtual barrier. At step F1c, data from the 3D camera, motion and/or sound sensors can be continuously sent to a computerized skeletal tracking system, preferably at all times while the system is being used for monitoring. At step F1d, a continuous video feed can be sent to the central monitoring primary display, preferably at all times while the system is being used for monitoring.

At step F1e, if the computerized skeletal tracking system does not detect a patient's skeleton because, for non-limiting example, the patient is covered with a sheet, blanket, or tray, is obscured by a caretaker or other individual, or for another reason, then the computerized skeletal tracking system continues to try to identify the patient until the obstruction is removed or the issue is resolved. In some embodiments, if the computerized skeletal tracking system does not detect a patient's skeleton within a preprogrammed, configurable length of time, then the computerized virtual blob detection monitoring system is activated and begins to monitor the patient (see e.g., FIGS. 2 and 4). In some embodiments, the computerized virtual blob detection monitoring system runs concurrently with the computerized skeletal tracking system. This preprogrammed, configurable length of time can be created or selected by the user and/or can be programmed through a software application stored on the computerized skeletal tracking system.

At step F1f, if the computerized skeletal tracking system detects that the patient or any part of the patient crosses the virtual barrier around the patient and/or the patient's bed, the skeletal monitoring system will alert the computerized communication system. A record can also be entered in a database to record the incident if other individuals, such as a caregiver, are also detected within the monitored room at the time virtual barrier is crossed. The system can be designed or programmed such that no alert is generated when another individual is detected, and it will continue to monitor the data being sent from the 3D camera, motion, and sound sensor. In this situation, generating an alarm/alert could result in a false alarm because there are other individual(s) with the patient, and such person(s) may be responsible for monitoring the patient and/or (even if not responsible) can assist the patient who is falling. Additionally, the person in the room should be in a better position to assist the patient as compared to the individual located at the central monitoring station. It is also within the scope of the disclosure to send alarm/alerts even if other individual(s) are in the room with the patient, as those individuals may not be the person responsible, may be elderly, may have a physical handicap preventing them from stopping a patient from falling, etc.

At step F1g, the computerized communication system preferably can first issue a verbal warning to the patient that they have crossed the virtual barrier. This verbal warning can be a pre-recorded message, including, but not limited to, a pre-recorded message from any caregiver, and will advise the patient to exit the virtual barrier and return to their previous position. At step F1h, should the patient fail to exit the virtual barrier and return to their previous position in a timely manner, an alert can be generated on the central monitoring alert display system (see e.g., FIG. 3). The system database can also be updated to reflect actions taken. The system can be designed to provide visual and/or audio alerts.

At step F1i, the computerized communication system can notify caregivers or other designated persons that the individual being monitored requires assistance. Notification of caregivers can be made through phone call, text messaging, speakerphone systems, pagers, email, or other electronic means of communication if so desired and configured. At step F1j, if the patient exits the virtual zone (i.e., crosses the virtual barrier), the system database can be updated to reflect such. Additionally, the system will continue to monitor the patient and store all data in the system database.

Figure 2:
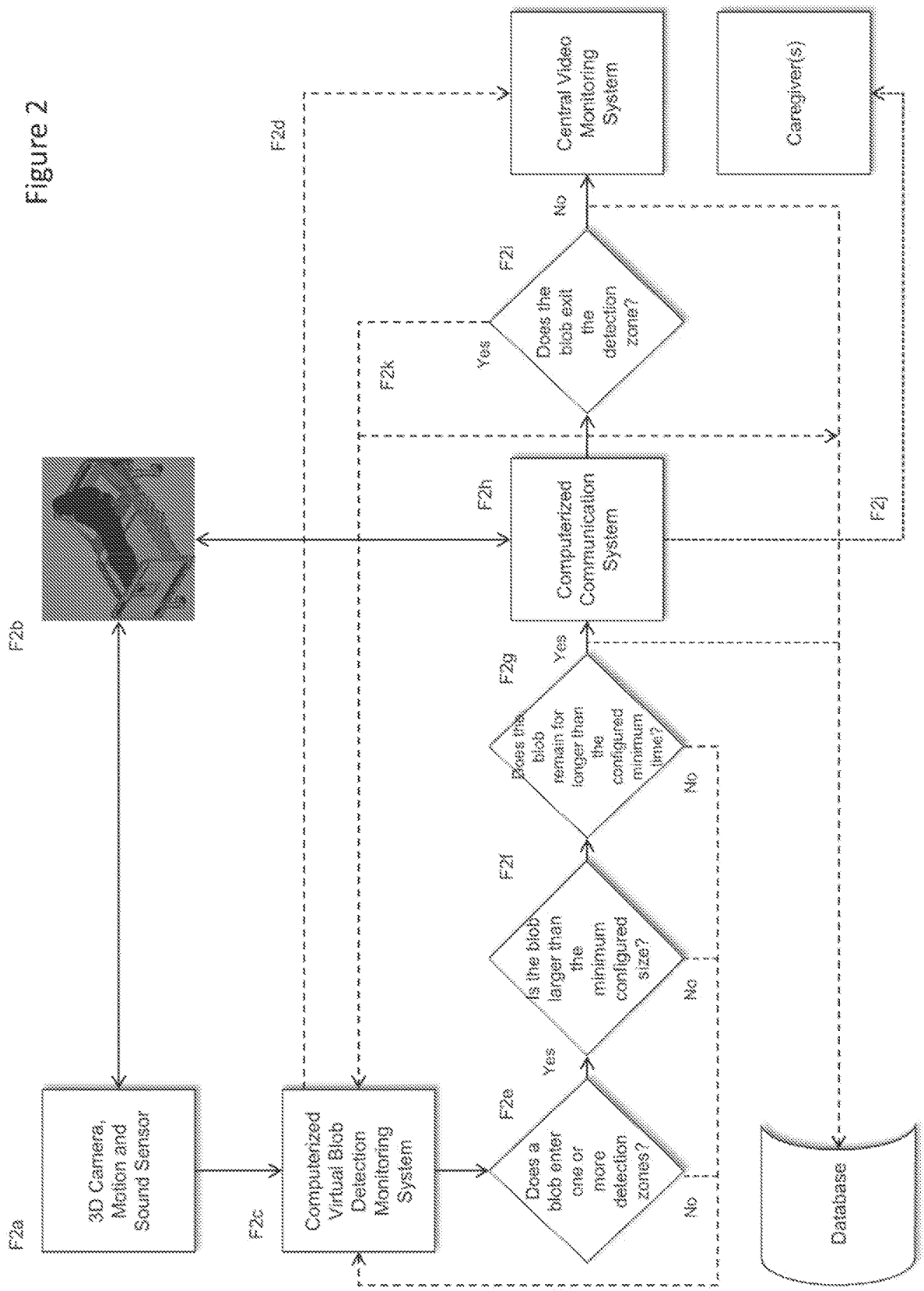
FIG. 2 is a block diagram of a virtual blob detection zone configuration, monitoring and alerting system and method in accordance with an embodiment of the present invention.

FIG. 2 illustrates a block diagram for the virtual blob detection zone configuration, monitoring, and alerting system and method of the disclosed system and method. Specifically, FIG. 2 shows the workflow for monitoring an individual's status through the use of one or more 3D camera, motion, and sound sensors.

At step F2a, one or more 3D camera, motion and/or sound sensors can be installed in the patient's or individual's room. At step F2b, the one or more 3D camera, motion, and sound sensors can be configured to recognize the area being monitored using three-dimensional areas as defined by x, y, and z coordinates in relation to the 3D camera, motion and/or sound sensor. Based on the data sent/captured by the 3D camera, motion and/or sound sensor(s), the computerized virtual blob detection monitoring system is programmed to recognize any 3D object within the configured area. The patient's body is recognized and tracked as one or more blobs. Virtual blob detection zones can also be calibrated at this time. At step F1c, data from the 3D camera, motion, and sound sensors can be continuously sent to a computerized virtual blob detection monitoring system, preferably at all times while the system is being used for monitoring. At step F1d, a continuous video feed can be sent to the central monitoring primary display, preferably at all times while the system is being used for monitoring.

At step F2e, if the computerized virtual blob detection monitoring system does not detect that the patient or any part of the patient (i.e. presented as a blob object(s)) has crossed into the designated virtual blob detection zone, it will continue monitoring. As a non-limiting example, if both hands of the patient enter the blob detection zone, the system may display and/or track as two different blobs or possibly as a single blob depending on how close the hands are to each other. If the computerized virtual blob detection monitoring system detects that the patient or any part of the patient has crossed into the designated virtual blob detection zone, it will then proceed to step F2f to determine how large the portion of the patient's body that entered the blob detection zone is. If the size of the patient's body that entered the blob detection zone is less than the configured minimum size, it will continue to monitor. Configuration is preferably through the detection system's programmed software and may be similar to how the zones, trip wires, etc. are configured. However, if the size of the patient's body that is within the blob detection zone is above the minimum predetermined or preprogrammed threshold for the object size, it can then proceed to step F2g. At step F2g, the system determines how long the patient's body or part of the patient's body has remained within the blob detection zone. If the patient's body or part of the body has not remained in the detection zone for greater than a configured amount of time, preferably no alert is generated and the system continues to monitor the individual. However, the system can also be programmed to issue/generate an alert based solely on the system detecting a large enough blob within the detection zone for any period of time and such is also considered within the scope of the disclosure. However, if at step F2g, the patient's body has remained within the blob detection zone for greater than the minimum configured time period, the monitoring system will alert the computerized communication system and can also enter a record of the incident in a database. If other individuals, such as a caregiver, are also detected within the monitored room at the time the virtual blob detection zone threshold is crossed, the system can be designed or programmed such that no alert is generated, and it will continue to monitor the data being sent from the 3D camera, motion, and sound sensor. In this situation, generating an alarm/alert could result in a false alarm because there are other individual(s) with the patient, and such person(s) may be responsible for monitoring the patient and/or (even if not responsible) can assist the patient who is falling. The person in the room may be in a better position to assist the patient as compared to the individual located at the central monitoring station. It is also within the scope of the disclosure to send alarm/alerts even if other individual(s) are in the room with the patient, as those individuals may not be the person responsible, may be elderly, may have a physical handicap preventing them from stopping a patient from falling, etc.

At step F2h, the computerized communication system preferably can first issue a verbal warning to the patient that he or she has entered the virtual blob detection zone. This verbal warning can be a pre-recorded message, including, but not limited to, a pre-recorded message from any caregiver, and will advise the patient to exit the virtual blob detection zone and return to his or her previous position. At step F2i, should the patient fail to exit the virtual blob detection zone and return to his or her previous position in a timely manner, an alert can be generated on the central monitoring alert display system (see e.g., FIG. 3). The system database can also be updated to reflect actions taken. The system can be designed to provide visual and/or audio alerts.

At step F2j, the computerized communication system can notify caregivers or other designated persons that the individual requires assistance. Notification of caregivers can be made through phone call, text messaging, speakerphone systems, pagers, email, or other electronic means of communication if so desired and configured. At step F2k, if the patient exits the virtual blob detection zone, the system database can be updated to reflect such. Additionally, the system will continue to monitor the patient and store all data in the system database.

Figure 3:
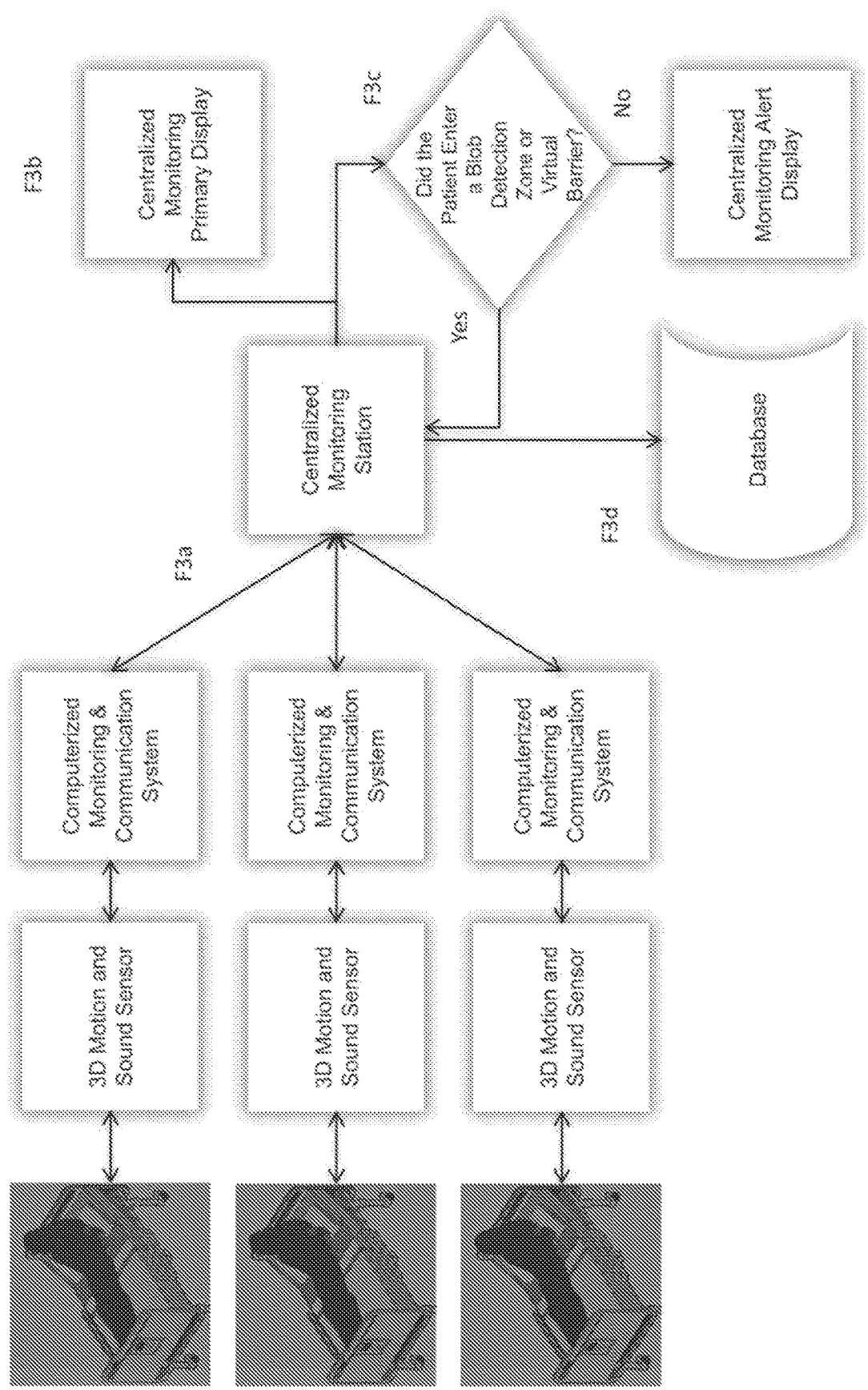
FIG. 3 is a block diagram of the centralizing monitoring and alerting system in accordance with an embodiment of the disclosure.

FIG. 3 illustrates a block diagram for centralized monitoring and alerting and shows the workflow for centralized monitoring and alerting of the central monitoring system regarding whether an individual has entered a virtual blob detection zone through the use of 3D camera, motion, and sound sensors. At step F3a, one or more 3D camera, motion, and sound sensors are installed in and/or just outside an individual's room, home, hospital room, or other place of temporary or permanent residence and are connected to the computerized monitoring and communication systems as described in FIGS. 1 and 2. The video, audio, and alert data can be sent to a centralized monitoring station where the data is aggregated. Preferably, the centralized monitoring station receives data at all times from the sensors to allow the various individuals to be constantly monitored at the centralized station regardless of whether or not an individual has entered a virtual blob detection zone.

At step F3b, all video, audio and alert feeds received by the centralized monitoring station can be displayed on the centralized monitoring primary display. Alternatively, multiple centralized monitoring primary displays can be utilized based on the quantity of rooms to be monitored at a given time. At step F3c, when the centralized monitoring system receives an alert from any of the computerized monitoring and communication systems indicating that an individual in any of the monitored rooms or other locations has fallen or otherwise entered into a virtual detection zone, the video, audio, and alert information for the specific room and/or individual is displayed on the centralized monitoring alert display. Should the centralized monitoring station receive alerts from more than one of the computerized monitoring and communication systems indicating that an individual in a monitored room or location has entered a virtual barrier or virtual blob detection zone, the centralized monitoring alert display may display the video, audio, and alerting information from all such instances preferably at the same time. If no alert is received by the centralized monitoring station, preferably nothing is displayed on the centralized monitoring alert display. At step F3d, an electronic record of any alerts received by the centralized monitoring station can be stored in an electronic database, which is in communication with the centralized monitoring station.

Figure 4:
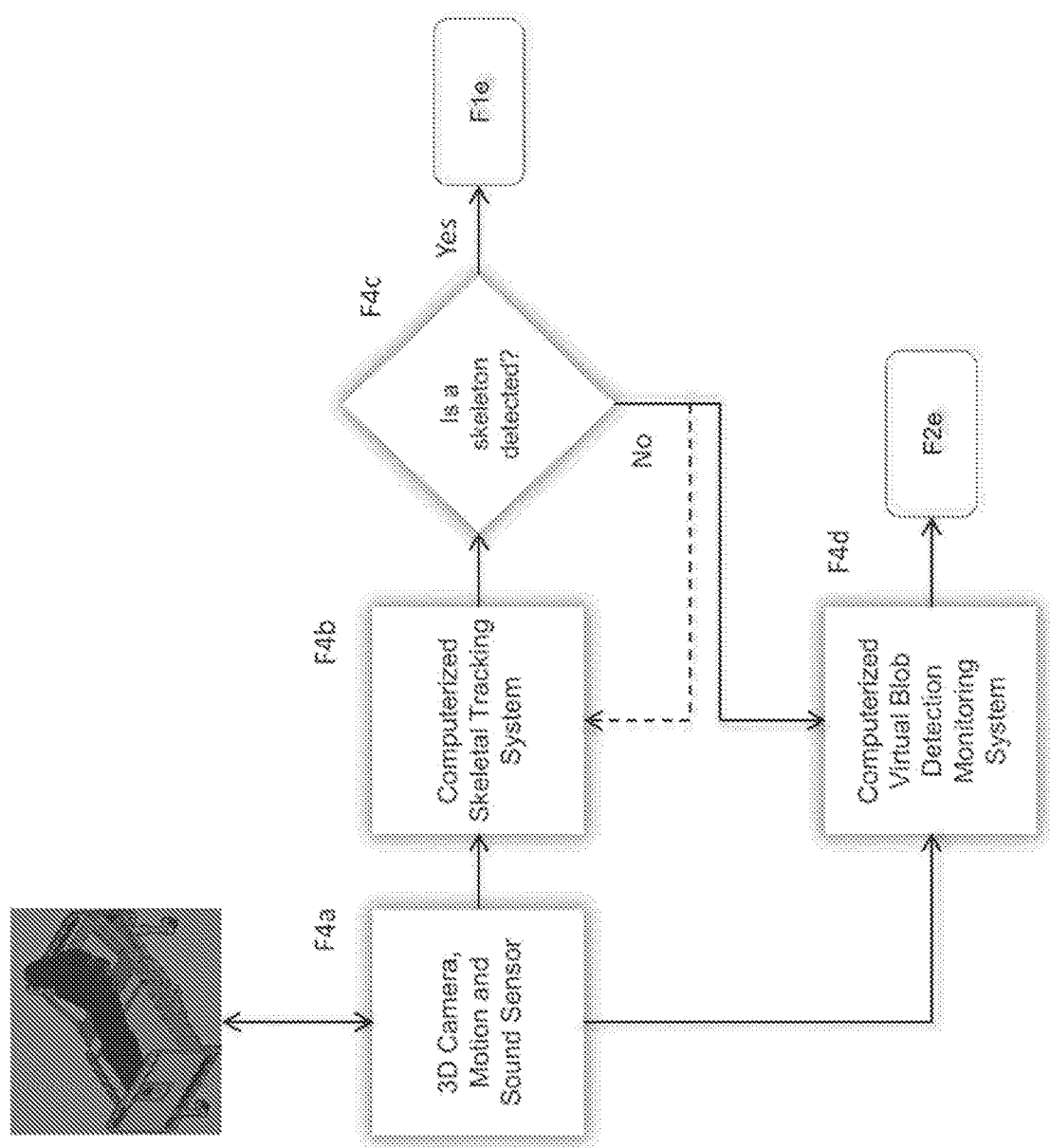
FIG. 4 is a block diagram of one embodiment illustrating how the computerized skeletal tracking system and virtual blob detection systems can be used separately and/or concurrently in accordance with an embodiment of the present invention.

FIG. 4 illustrates a block diagram for how a computerized skeletal tracking system and a virtual blob detection monitoring system can be used concurrently or independently in the disclosed system and method. At step F4a, one or more 3D camera, motion, and sound sensors are installed in and/or just outside an individual's room, home, hospital room, or other place of temporary or permanent residence and are connected to the computerized monitoring and communication systems as described in FIGS. 1, 2 and 3. The video, audio and/or alert data can be sent to a centralized monitoring station where the data is aggregated. Preferably, the centralized monitoring station receives data at all times from the sensors to allow the various individuals to be constantly monitored at the centralized monitoring station regardless of whether or not an individual has entered a virtual barrier or virtual blob detection zone. At step F4b, in some embodiments, both the computerized skeletal tracking system and the computerized virtual blob detection systems operate independently. In these embodiments, the computerized skeletal tracking system performs as described in FIG. 1, and the computerized virtual blob detection monitoring system performs concurrently as described in FIG. 2. In these embodiments, it is possible that information between the two systems may conflict. As a non-limiting example, if a hospital food tray is passed to a patient and remains within the blob detection zone for longer than the configured minimum time, the computerized virtual blob detection system may register an alert, while the computerized skeletal tracking system may not. The user can select which system (if any) would take priority through a software application stored on the computerized skeletal tracking system and/or the computerized virtual blob detection monitoring system. Also, an alert can be generated only when both systems independently generate an alert, or in the alternative, an alert may be generated in the event either system generates an alert. In other embodiments, the computerized virtual blob detection monitoring system is only used when the computerized skeletal tracking system fails to identify a patient or skeleton.

Additionally, the functions of the computerized virtual blob detection monitoring system and the computerized skeletal tracking system can be performed in practice by a single system. In these embodiments, the disclosure performs the same processes described in FIGS. 1-4, but a single combined system replaces the computerized skeletal tracking system and computerized virtual blob detection monitoring system.

At step F4c, in some embodiments, if the computerized skeletal tracking system detects a skeleton, then the method proceeds to step F1e of FIG. 1. It the computerized skeletal tracking system does not detect a skeleton within a preprogrammed, configurable length of time, then the computerized virtual blob detection monitoring system can be activated. This preprogrammed, configurable length of time can be created by the user through a software application stored on the computerized skeletal tracking system. In some embodiments, while the computerized virtual blob detection monitoring system is in use, the computerized skeletal tracking system may continue to try to detect a patient. If a patient is detected, the process proceeds to F1e of FIG. 1. At step F4d, the process then proceeds to step F2e of FIG. 2.

Figure 5:

FIGS. 5 through 17 illustrate several set up screen shots for configuring the bed zone, virtual rails (trip wires), virtual blob detection zones and alert types. In FIG. 5, the bed zone, virtual trip wires, and virtual blob detection zones can be configured for a given or specific 3D camera, motion, and sound sensor. To begin configuration, the user can hover over the 3D camera, motion, and sound sensor video window with the cursor, right-click, select the plugin, and then select configure plug-in. A window will popup showing the 3D camera, motion, and sound sensors' feed (see e.g., FIG. 6). The user selects the icon for the type of zone or rail the user wishes to draw, which as a non-limiting example and illustrative purposes, can be a bed zone, virtual rail (trip wires), and virtual blob detection zone(s) (see e.g., FIG. 7).

As non-limiting examples, the icons that appear on the screen for selection can include the following symbols shown in FIG. 7. In this non-limiting example, in no particular order, some of the icons include Bed Zone, Auto Bed Zone (Select Patient), Auto Bed Zone (Auto-select), Saved Zones, Virtual Rail (Trip Wires), Virtual Blob Detection Zone and Clear All.

Figure 6:
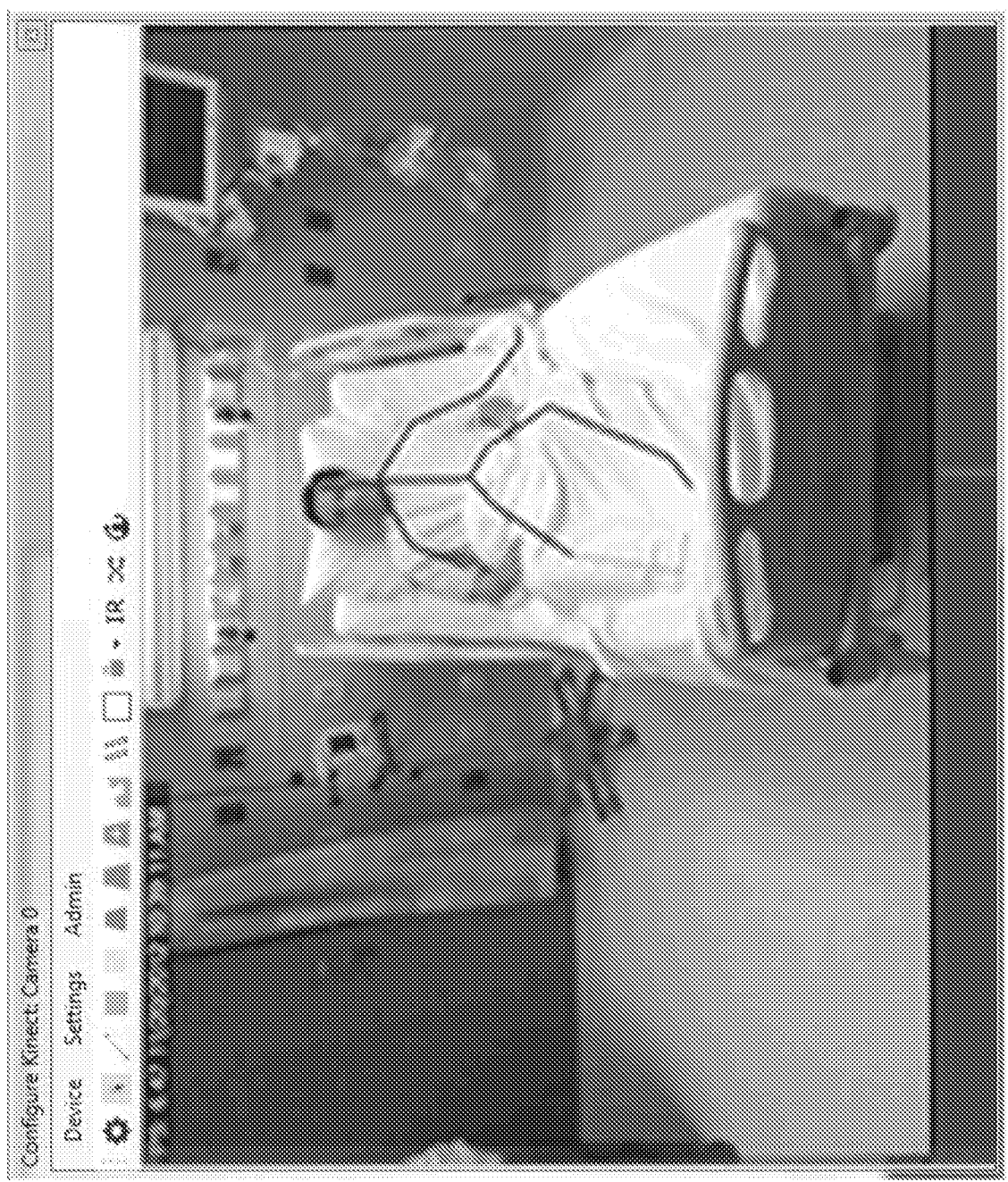
Figure 8:
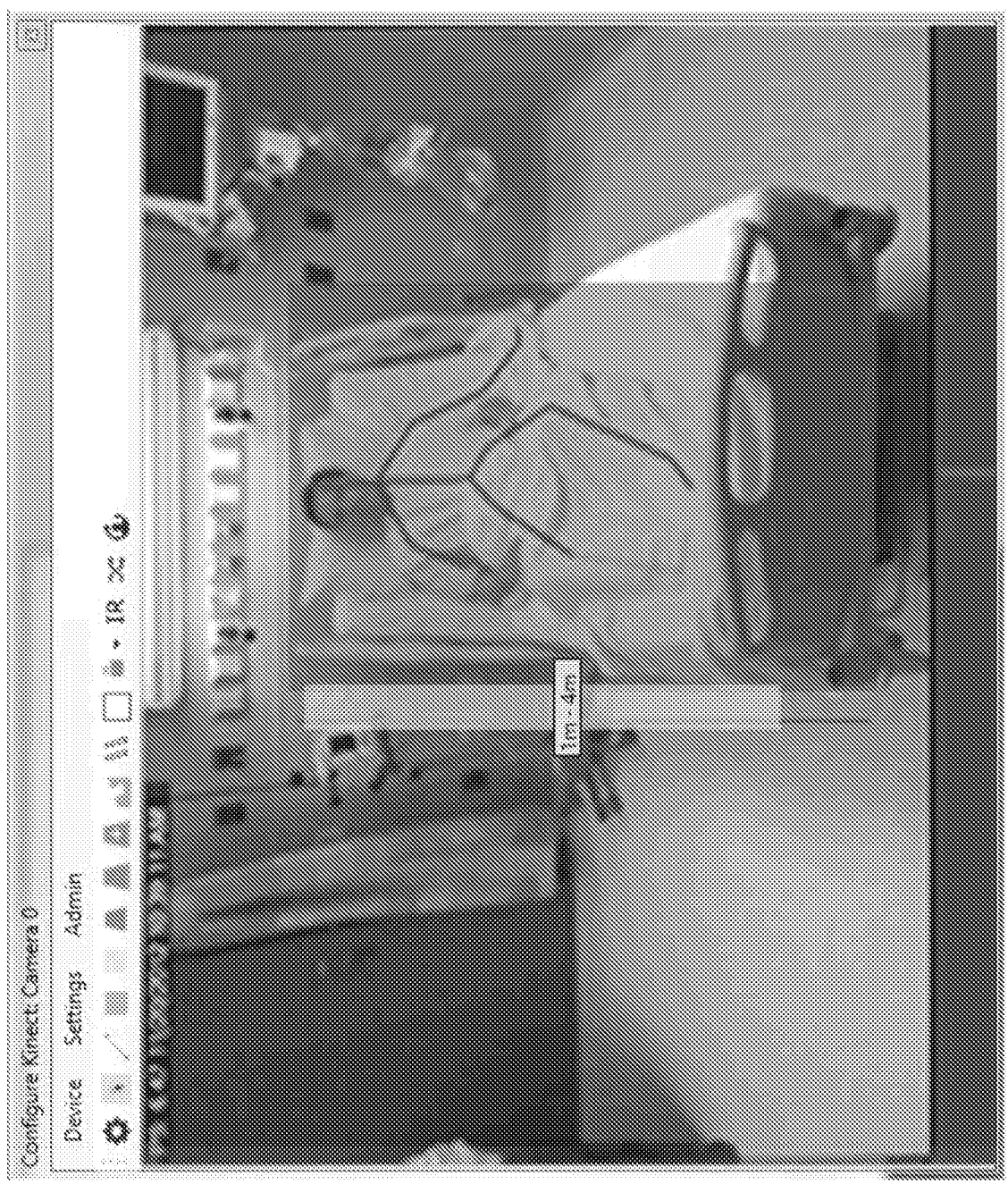
Figure 10:
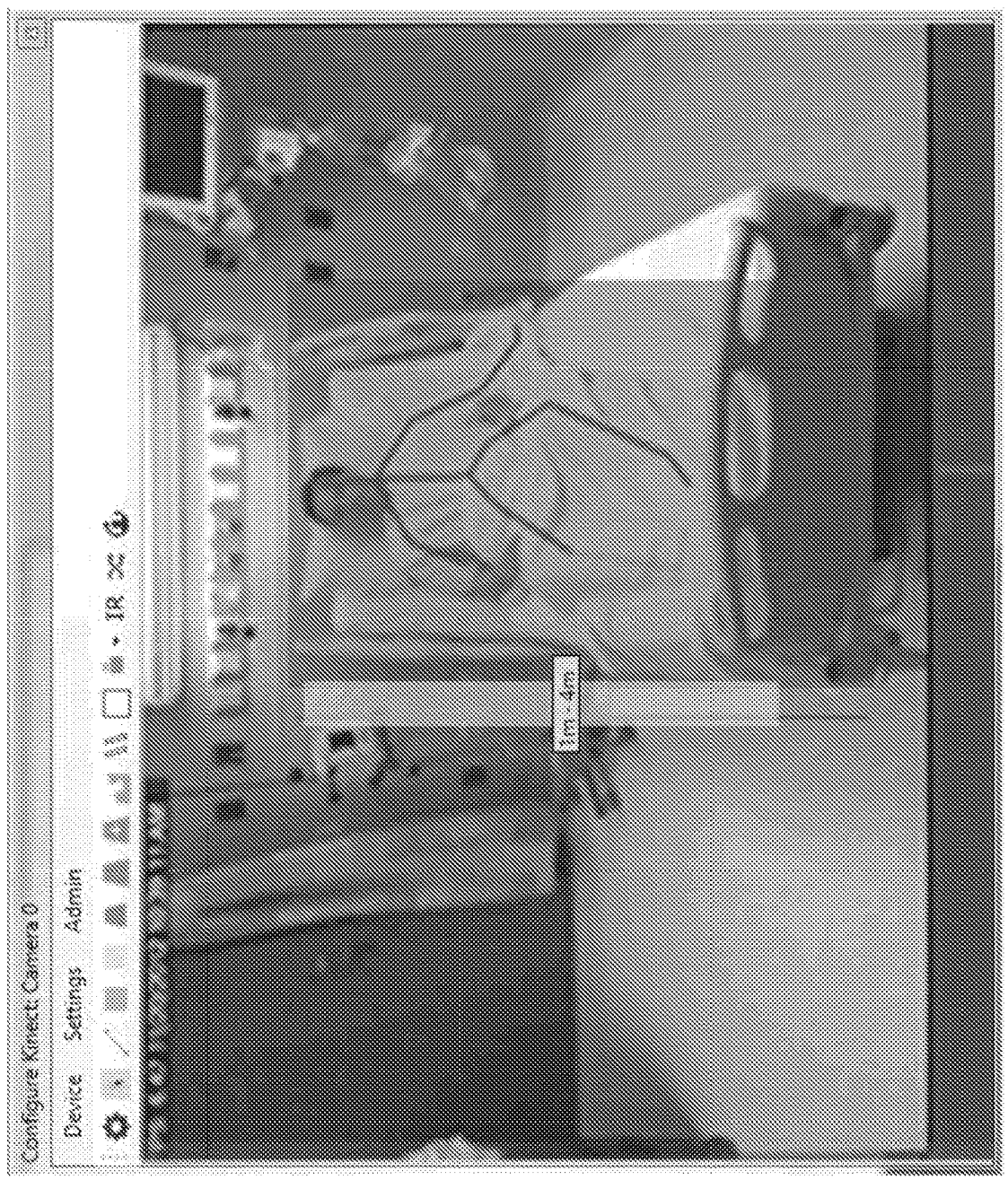

As seen in FIG. 6, to place a zone, the user clicks on the screen where he or she would like to start the zone. Then, the cursor is moved to the corner point for zone and clicked again. The user continues to select additional points until the zone is drawn to the user's satisfaction. Preferably, the user clicks on the round end point of the beginning of the zone to complete the zone (see e.g., FIG. 6). When the zone has been completed, the zone can appear, and a depth range box (i.e. square, rectangle, etc. disposed over the patient on the screen) can be provided on the screen, such as, but not limited to, in the middle of the screen or zone (see e.g., FIG. 8), though any location on the screen is considered within the scope of the invention. Placing a virtual rail is done with a similar process wherein the user clicks on the screen where he or she would like to start the rail. Then, the cursor is moved to the end point for the rail, and the user clicks on the screen again to place the rail. As seen in FIG. 10, upon completion of this process, the zone and/or rail(s) appear and have a depth range box, preferably in the middle.

Figure 9:
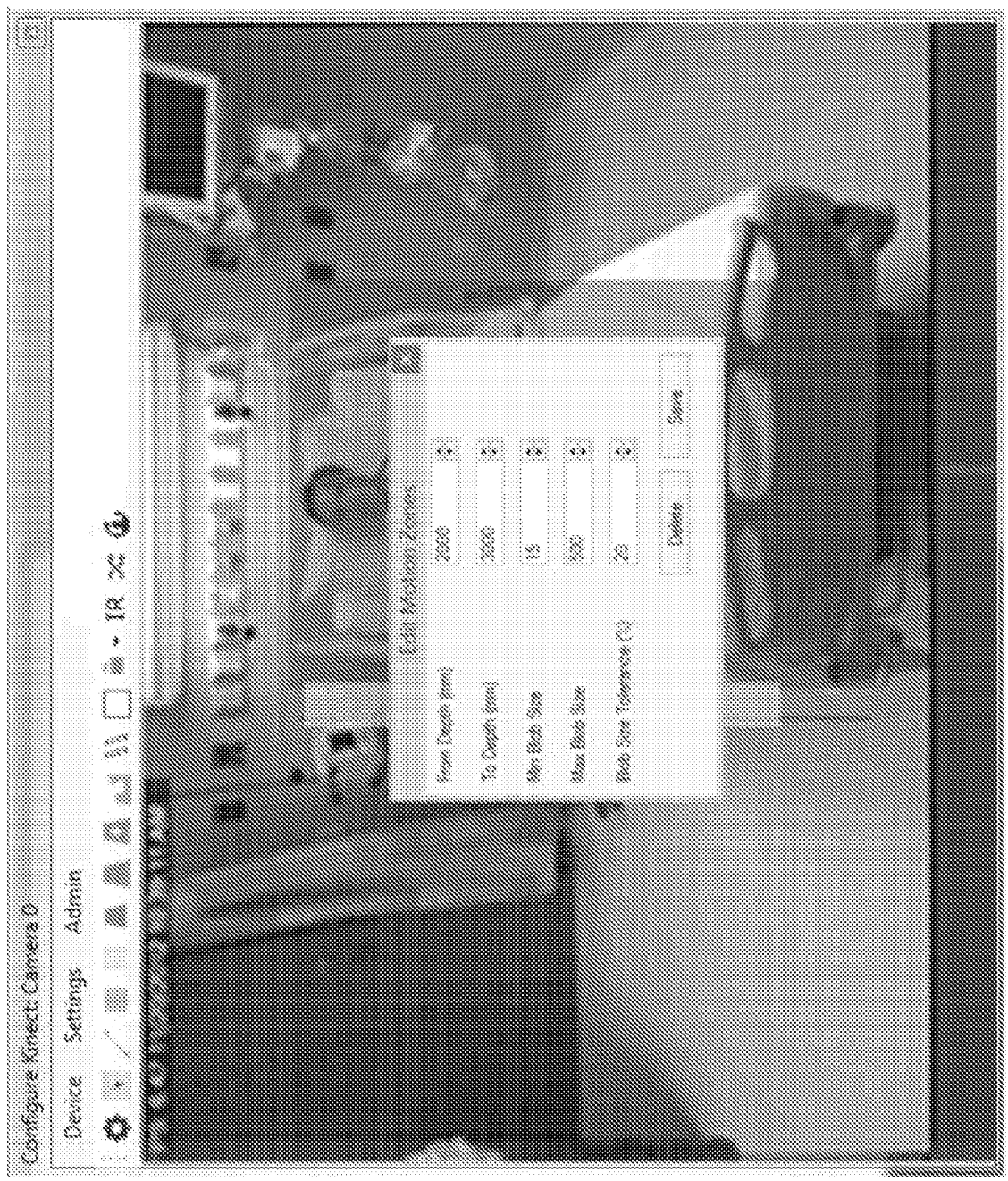

As seen in FIG. 9, the user can adjust the depth range for any given zone or rail. By preferably double clicking on the depth range box or by other conventional selection methods an Edit Depth window can appear. The user can enter in the depth ranges (preferably in millimeters (mm) though not considered limiting). Additionally, the user can enter in minimum and maximum 3D object sizes (preferably in square root pixels though not considering limiting) to detect entering the virtual blob detection zones as well as a tolerance for the size change of an object. The user can click Save button or icon when done to store the entered values.

If there are any other types of zones or rails to draw for the particular sensor, the above steps are repeated to place the next zone or rail and the depth setting can be adjusted for each if necessary. Additionally, all zones and rails can be cleared by clicking on or otherwise selecting the Clear All icon in the toolbar. Once all of the zones/rails are configured, the user can close the window to finish, or the user may have the option to save the zone/rail configuration for later use.

Figure 11:

As seen in FIG. 11, to access the main settings window, the user can click or otherwise select the Settings menu and then select Main Settings from the drop-down list. As one non-limiting alternative, the user can click on the Gear icon or other designated icon in the toolbar to access the main settings window.

Figure 12:
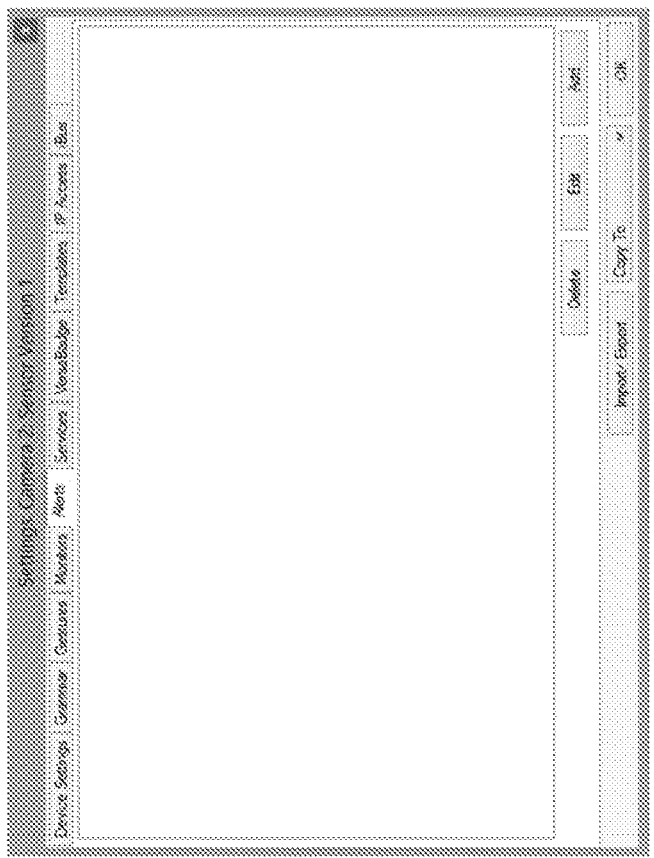
Figure 13:
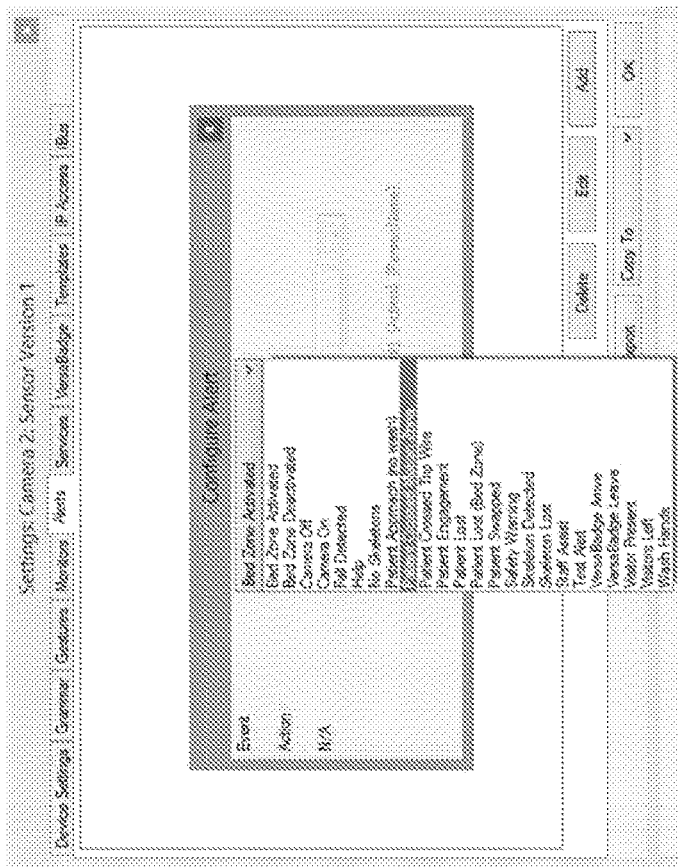
Figure 14:
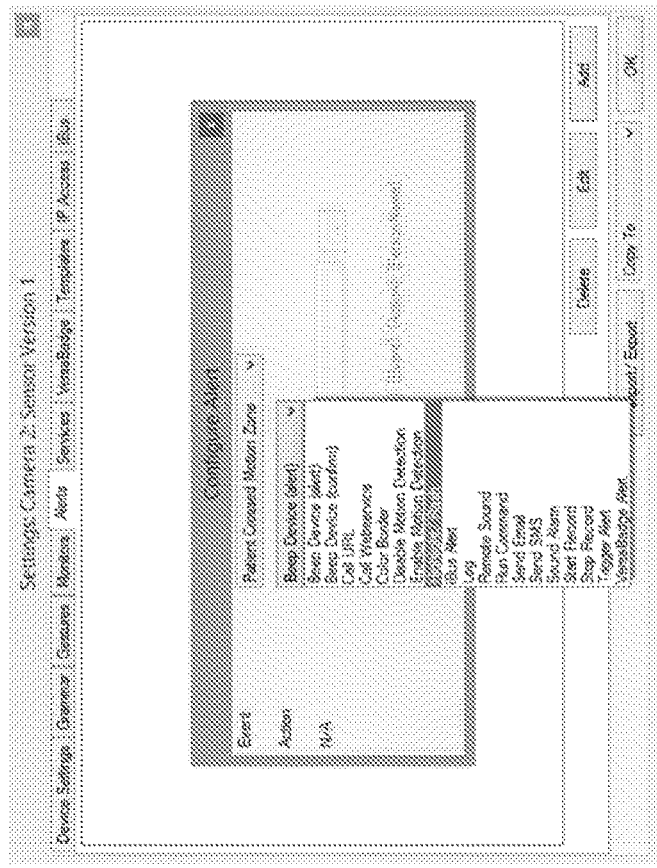
Figure 15:
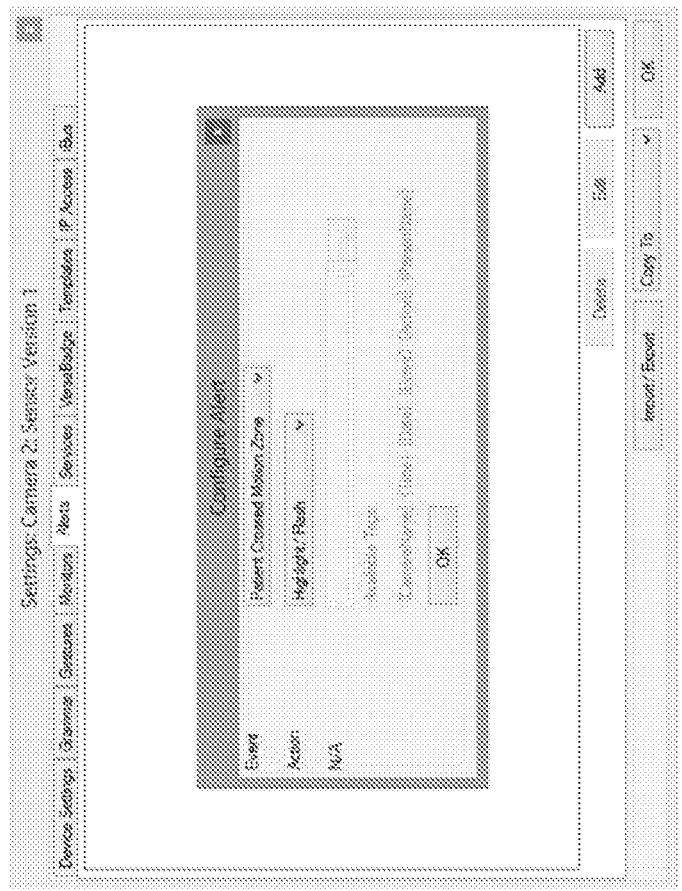
Figure 16:
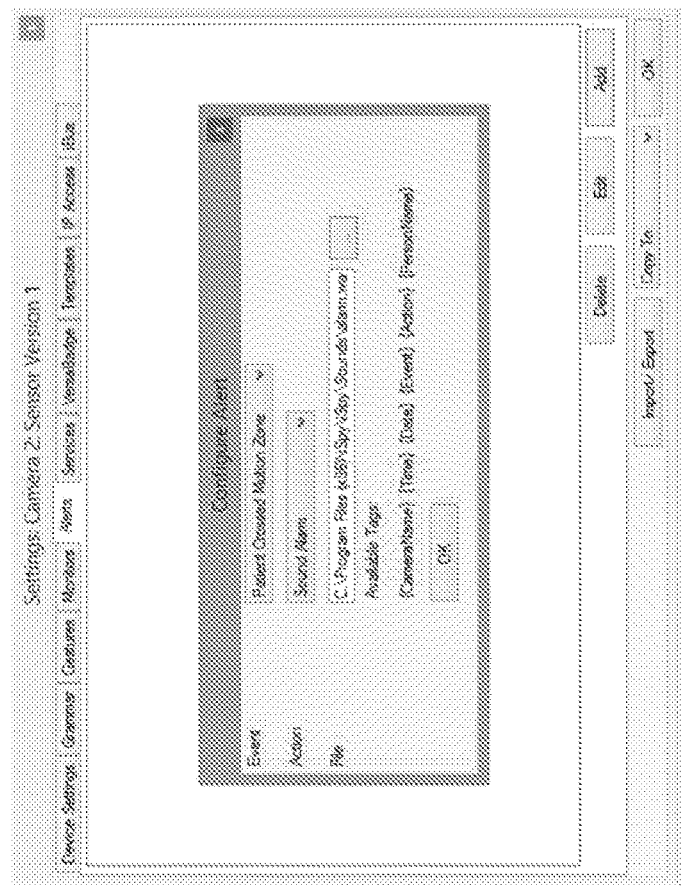
Figure 17:
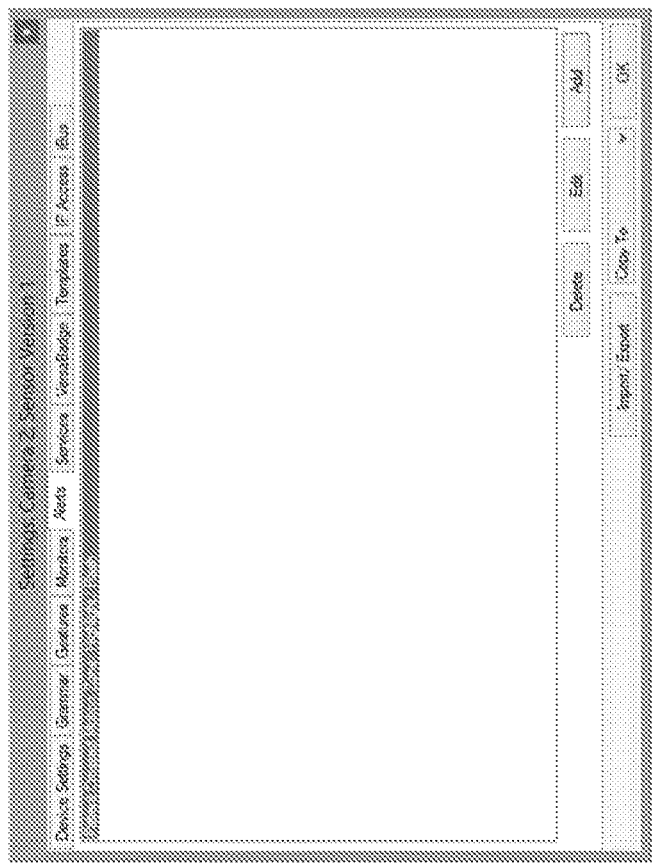

As seen in FIG. 12, for one non-limiting way to configure a new Alert, the user can select the Alerts tabs and then click on or otherwise select the Add button, which can result in the Configure Alert box appearing on the screen (see e.g., FIG. 13). As seen in FIG. 13, under the Event field, the user can then select the event from the drop down list that the user wishes to send an alert on.

As seen in FIG. 13, once the Event type is selected, under the Action field, the user can select the Action he or she wishes to have the system perform when the selected Event is detected. Once the Event and Action have been selected, the OK button (see e.g., FIG. 15) can be selected to save the selected entries.

For certain Actions, an additional field may need to be completed to finish the Action. If the field is required, it can appear below the Action dropdown (see e.g., FIG. 16). If no further fields are required, the Configure Alert box can display N/A (see e.g., FIG. 15) or just be blank. As mentioned above, once all settings are selected, the user clicks or otherwise selects the OK button, which causes the new Alert to be listed in the Alerts tab window. To edit an existing Alert, the user first clicks on or otherwise selects the Alert and then selects the Edit button (see e.g., FIG. 17). To delete an Alert, first highlight it can then click on the Delete button (see e.g., FIG. 17).

To add more Alerts, the user clicks or selects the Add button and repeats the above described steps. Once finished, the user clicks on or otherwise selects the bottom corner OK button to save and close the window.

Figure 18:
FIG. 18 is a non-limiting example of a centralized video monitoring system that can be used with the systems and method shown in FIGS. 1 through 3 in accordance with an embodiment of the present disclosure.

FIG. 18 shows a non-limiting example of a centralized video monitoring system that can be used with the system and method. The window highlighted in red is a non-limiting example of an alert that can be generated when the patient fails to return to within the perimeter of the virtual safety rails.

Figure 19:
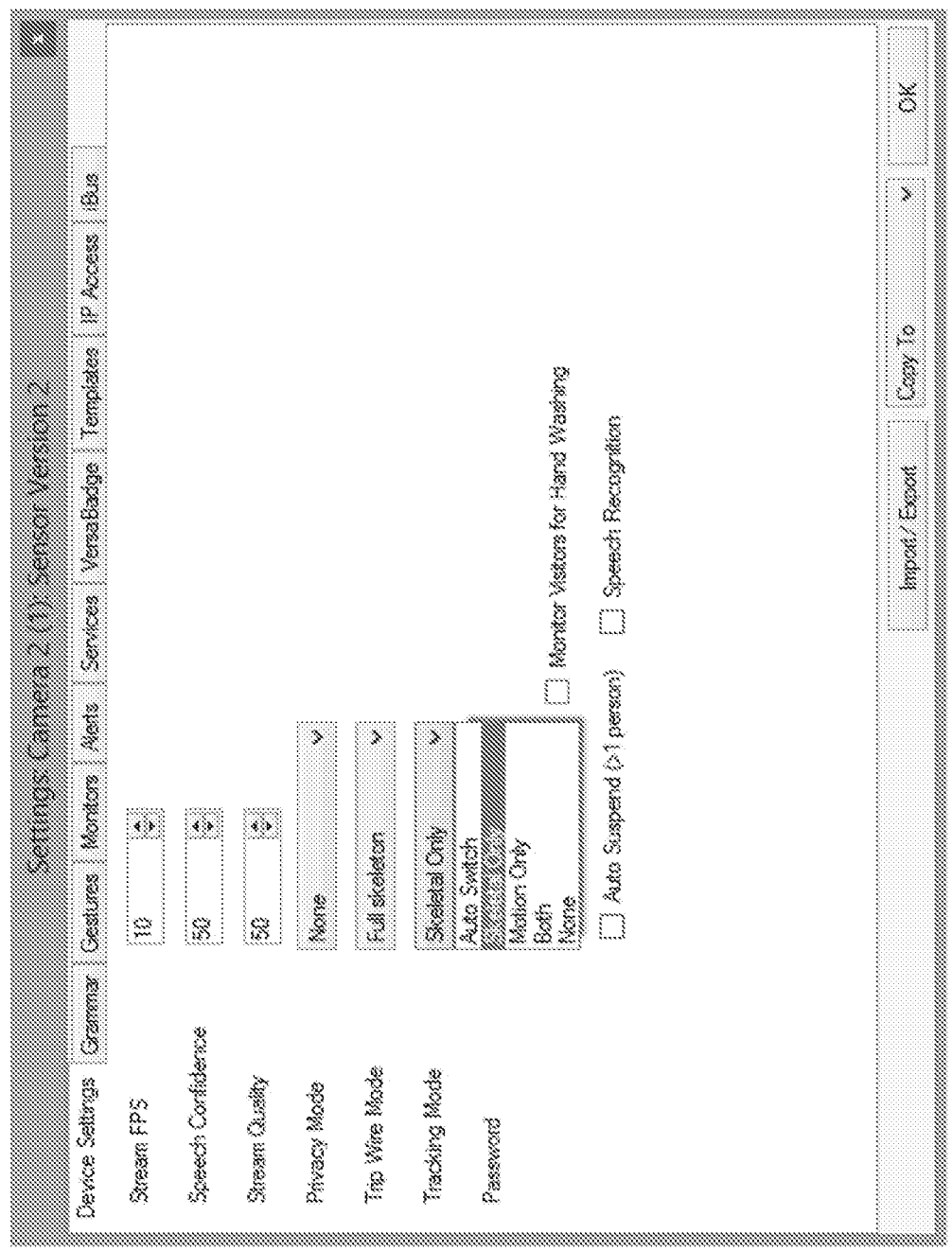
FIG. 19 is a non-limiting example illustrating how to configure the operational mode of the system in accordance with an embodiment of the present disclosure.

FIG. 19 shows a non-limiting example of how to configure the operational mode of the system. The user can select Auto-Switch in which the system will automatically switch between skeletal tracking and 3D blob detection depending on whether a skeleton is able to be tracked. Alternatively, the user may select both and cause the system to use both 3D Blob detection and skeletal tracking for alerting. Alternatively, the user can select to use either skeletal tracking or 3D blob detection solely or neither at all.

In one non-limiting embodiment, the disclosed system and method can use the following components:
1. One or more 3D camera, motion and/or sound sensors;
2. A computerized virtual blob detection monitoring system;
3. A computerized skeletal tracking system;
4. A computerized communication system;
5. A centralized monitoring primary display;
6. A centralized monitoring alert display; and
7. Database The various components can be in electrical and/or wireless communication with each other.

Located remote is defined to mean that the centralized monitoring station, centralized monitoring primary display and/or centralized monitoring alert display is not physically located within the monitored rooms. However, the location can be on the same premises at a different location (i.e. nurse station for the premises, hospital, etc.) or a different location (i.e. monitoring station, etc.).

The automatic detection of an individual entering a prescribed virtual blob detection zone will provide significant administrative and clinical benefits to caregivers and individuals alike, including the following non-limiting public benefits.
1. Automation of determination of perimeter violation and automated notification of caregivers and/or other designated entities and/or individuals.
2. Ability to alert patients, caregivers and other individuals in time to prevent a monitored patient from getting out of bed.
3. Reduction in response time for monitored individuals who have fallen and require assistance.
4. Increased survival rate for monitored individuals who have experienced a fall.
5. Reduction in costs for hospitalization and medical care related to complications from a fall.
6. Ability to distinguish multiple individuals and prevent false positives.
7. Ability to distinguish direction of motion to prevent false positives.
8. Ability to provide video feed of a monitored patient under all lighting conditions to the central video monitoring system.
9. Audio and gesture based recognition to allow multiple forms of communication with patient.

Any computer/server/electronic database system (collectively "computer system") capable of being programmed with the specific steps of the present invention can be used and is considered within the scope of the disclosure. Once specifically programmed, such computer system can preferably be considered a special purpose computer limited to the use of two or more of the above particularly described combination of steps (programmed instructions) performing two of more of the above particularly described combination of functions.

All components of the present disclosure system and their locations, electronic communication methods between the system components, electronic storage mechanisms, etc. discussed above or shown in the drawings, if any, are merely by way of example and are not considered limiting and other component(s) and their locations, electronic communication methods, electronic storage mechanisms, etc. currently known and/or later developed can also be chosen and used and all are considered within the scope of the disclosure.

Unless feature(s), part(s), component(s), characteristic(s) or function(s) described in the specification or shown in the drawings for a claim element, claim step or claim term specifically appear in the claim with the claim element, claim step or claim term, then the inventor does not consider such feature(s), part(s), component(s), characteristic(s) or function(s) to be included for the claim element, claim step or claim term in the claim when and if the claim element, claim step or claim term is interpreted or construed. Similarly, with respect to any "means for" elements in the claims, the inventor considers such language to require only the minimal amount of features, components, steps, or parts from the specification to achieve the function of the "means for" language and not all of the features, components, steps or parts describe in the specification that are related to the function of the "means for" language.

While the disclosure has been described and disclosed in certain terms and has disclosed certain embodiments or modifications, persons skilled in the art who have acquainted themselves with the disclosure will appreciate that it is not necessarily limited by such terms nor to the specific embodiments and modification disclosed herein. Thus, a wide variety of alternatives suggested by the teachings herein can be practiced without departing from the spirit of the disclosure, and rights to such alternatives are particularly reserved and considered within the scope of the disclosure.

What is claimed is:

1. A system for detecting when a monitored individual or any part of the monitored individual has crossed over a designated electronic perimeter, the system comprising:
    one or more 3D camera, motion, and sound sensors located in a room with an individual to be monitored and configured to capture video data of the individual within the room;
    a computerized monitoring system configured to:
        electronically receive video data from the one or more 3D camera, motion, and sound sensors;
        use skeletal tracking to electronically monitor the room for a crossing of a designated electronic perimeter by the individual based on the video data electronically received from the one or more 3D camera, motion, and sound sensors;
        use virtual blob detection to electronically monitor the room for the crossing of the designated electronic perimeter by the individual based on the video data electronically received from the one or more 3D camera, motion, and sound sensors;
        detect a conflict between determinations of whether the individual or part of the individual crossed the designated electronic perimeter made using skeletal tracking and virtual blob detection;
        resolve the conflict between the determinations made using skeletal tracking and virtual blob detection according to a predetermined setting; and
        based on resolution of the conflict, electronically transmit a determination that the individual or part of the individual has crossed the designated electronic perimeter.

2. The system of claim 1, wherein the predetermined setting prioritizes using skeletal tracking over using virtual blob detection, and wherein the determination that the individual or part of the individual has crossed the designated electronic perimeter that is electronically transmitted is made using skeletal tracking.

3. The system of claim 2, wherein the predetermined setting prioritizes using skeletal tracking over using virtual blob detection when the individual has previously been identified using skeletal tracking.

4. The system of claim 1, wherein the predetermined setting prioritizes using virtual blob detection over using skeletal tracking, and wherein the determination that the individual or part of the individual has crossed the designated electronic perimeter that is electronically transmitted is made using virtual blob detection.

5. The system of claim 1 further comprising a computerized communication system that is configured to receive an alert from the computerized monitoring system when the computerized monitoring system electronically detects that the individual or a part of the individual has crossed the designated electronic perimeter.

6. The system of claim 5, wherein the computerized monitoring system is configured to electronically alert the computerized communication system when the computerized monitoring system electronically detects that the individual or a part of the individual has crossed the designated electronic perimeter and remains in the designated electronic perimeter for a predetermined period of time.

7. The system of claim 6, wherein the computerized communication system is further configured to electronically issue an audible message to the individual to inform the individual that the individual has crossed the designated electronic perimeter.

8. The system of claim 1, further comprising a central monitoring alert display, wherein an alert is generated on the central monitoring alert display upon the computerized monitoring system electronically determining that the individual or part of the individual crossed the designated electronic perimeter.

9. The system of claim 1, wherein electronically transmitting the determination that the individual has crossed the designated electronic perimeter comprises notifying a designated person associated with the individual.

10. The system of claim 9, wherein notifying the designated person associated with the individual is further based on determining that the individual remains in the designated electronic perimeter for at least a predetermined period of time.

11. A computerized method for detecting when a monitored individual or any part of the monitored individual has crossed over a designated electronic perimeter, the method comprising:
    electronically receiving video data from one or more 3D camera, motion, and sound sensors that are configured to capture video data of an individual being monitored;
    using skeletal tracking to electronically monitor the room for a crossing of a designated electronic perimeter by the individual based on the video data electronically received from the one or more 3D camera, motion, and sound sensors;
    using virtual blob detection to electronically monitor the room for the crossing of the designated electronic perimeter by the individual based on the video data electronically received from the one or more 3D camera, motion, and sound sensors;

detecting a conflict between determinations of whether the individual or part of the individual crossed the designated electronic perimeter made using skeletal tracking and virtual blob detection;

resolving the conflict between the determinations made using skeletal tracking and virtual blob detection according to a predetermined setting; and based on resolution of the conflict, electronically transmitting a determination that the individual or part of the individual has crossed the designated electronic perimeter.

12. The computerized method of claim 11, wherein the predetermined setting prioritizes using skeletal tracking over using virtual blob detection, and wherein the determination that the individual or part of the individual has crossed the designated electronic perimeter that is electronically transmitted is made using skeletal tracking.

13. The computerized method of claim 12, wherein the predetermined setting prioritizes using skeletal tracking over using virtual blob detection when the individual has previously been identified using skeletal tracking.

14. The computerized method of claim 11, wherein the predetermined setting prioritizes using virtual blob detection over using skeletal tracking, and wherein the determination that the individual or part of the individual has crossed the designated electronic perimeter that is electronically transmitted is made using virtual blob detection.

15. The computerized method of claim 11, wherein electronically transmitting the determination that the individual has crossed the designated electronic perimeter comprises transmitting an alert to a computerized communication system.

16. The computerized method of claim 15, wherein the alert to the computerized communication system is transmitted upon determining that the individual or part of the individual has remained in the designated electronic perimeter for at least a predetermined period of time.

17. The computerized method of claim 15, wherein the computerized communication system is further configured to transmit the determination to a central monitoring alert display, wherein an alert is generated on the central monitoring alert display.

18. The computerized method of claim 11, wherein electronically transmitting the determination that the individual or part of the individual has crossed the designated electronic perimeter comprises electronically issuing an audible message to the individual to inform the individual that the individual has crossed the designated electronic perimeter.

19. The computerized method of claim 11, wherein electronically transmitting the determination that the individual has crossed the designated electronic perimeter comprises notifying a designated person associated with the individual.

20. The computerized method of claim 19, wherein notifying the designated person associated with the individual is further based on determining that the individual remains in the designated electronic perimeter after a predetermined period of time.

* * * * *

UNITED STATES PATENT AND TRADEMARK OFFICE
CERTIFICATE OF CORRECTION

PATENT NO. : 10,629,046 B2  
APPLICATION NO. : 16/166857  
DATED : April 21, 2020  
INVENTOR(S) : Neil Kusens Page 1 of 1

It is certified that error appears in the above-identified patent and that said Letters Patent is hereby corrected as shown below:

In the Specification

Column 01, Line 52: Please remove "Motion" and replace with --Motion,--.

Column 03, Line 71: Before "3D" please insert --the--.

Signed and Sealed this  
Twenty-sixth Day of May, 2020

Andrei Iancu  
*Director of the United States Patent and Trademark Office*